(12) United States Patent
Hawkins et al.

(10) Patent No.: US 10,456,485 B1
(45) Date of Patent: *Oct. 29, 2019

(54) SINGLE-EMITTER LIGHTING DEVICE THAT OUTPUTS A MINIMUM AMOUNT OF POWER TO PRODUCE INTEGRATED RADIANCE VALUES SUFFICIENT FOR DEACTIVATING PATHOGENS

(71) Applicant: KENALL MANUFACTURING COMPANY, Kenosha, WI (US)

(72) Inventors: James W. Hawkins, Lake Forest, IL (US); Nathan D. Heiking, Pleasant Prairie, WI (US)

(73) Assignee: KENALL MANUFACTURING COMPANY, Kenosha, WI (US)

( * ) Notice: Subject to any disclaimer, the term of this patent is extended or adjusted under 35 U.S.C. 154(b) by 268 days.

This patent is subject to a terminal disclaimer.

(21) Appl. No.: 15/485,926

(22) Filed: Apr. 12, 2017

Related U.S. Application Data

(63) Continuation of application No. 15/178,349, filed on Jun. 9, 2016, now Pat. No. 9,700,641.

(Continued)

(51) Int. Cl.
*A61L 2/08* (2006.01)
*A61L 9/18* (2006.01)
(Continued)

(52) U.S. Cl.
CPC .............. *A61L 2/084* (2013.01); *A61L 9/18* (2013.01); *H05B 33/089* (2013.01);
(Continued)

(58) Field of Classification Search
CPC .......... A61L 2/084; A61L 9/18; H05B 33/089
See application file for complete search history.

(56) References Cited

U.S. PATENT DOCUMENTS

| | | | |
|---|---|---|---|
| 3,670,193 | A | 6/1972 | Thorington et al. |
| 3,992,646 | A | 11/1976 | Corth |

(Continued)

FOREIGN PATENT DOCUMENTS

| | | |
|---|---|---|
| CN | 101248534 A | 8/2008 |
| CN | 101331430 A | 12/2008 |

(Continued)

OTHER PUBLICATIONS

"Continuous Environmental Disinfection in the OR: A Case Study", Maury Regional Medical Center (publicly available as of the filed of application).

(Continued)

*Primary Examiner* — Kevin Joyner
(74) *Attorney, Agent, or Firm* — Marshall, Gerstein & Borun LLP; Randall G. Rueth

(57) ABSTRACT

A lighting device configured to deactivate dangerous pathogens (e.g., MRSA bacteria) in an environment. The lighting device includes at least one lighting element with a single light source configured to provide light. At least a first component of the light comprising light having a wavelength of about 405 nm, and at least a second component of the light comprising light having a wavelength of greater than 420 nm. The first component of light has a minimum integrated irradiance of 0.01 mW/cm$^2$ measured from any unshielded point in the environment that is 1.5 m from any point on any external-most luminous surface of the lighting device.

21 Claims, 27 Drawing Sheets

Related U.S. Application Data

(60) Provisional application No. 62/190,113, filed on Jul. 8, 2015, provisional application No. 62/185,391, filed on Jun. 26, 2015.

(51) Int. Cl.
*H05B 33/08* (2006.01)
*H05B 37/02* (2006.01)
*H01L 33/50* (2010.01)

(52) U.S. Cl.
CPC ...... *H05B 37/0245* (2013.01); *A61L 2202/25* (2013.01); *H01L 33/505* (2013.01)

(56) References Cited

U.S. PATENT DOCUMENTS

| | | |
|---|---|---|
| 5,189,393 A | 2/1993 | Hu |
| 6,242,752 B1 | 6/2001 | Soma et al. |
| 6,791,259 B1 | 9/2004 | Stokes et al. |
| 7,658,891 B1 | 2/2010 | Barnes |
| 8,398,264 B2 | 3/2013 | Anderson et al. |
| 8,476,844 B2 | 7/2013 | Hancock et al. |
| 8,508,204 B2 | 8/2013 | Deurenberg et al. |
| 9,039,966 B2 | 5/2015 | Anderson et al. |
| 9,046,227 B2 | 6/2015 | David et al. |
| 9,368,695 B2 | 6/2016 | David et al. |
| 9,439,989 B2 | 9/2016 | Lalicki et al. |
| 9,581,310 B2 | 2/2017 | Wu et al. |
| 9,700,641 B2 | 7/2017 | Hawkins et al. |
| 2002/0175815 A1 | 11/2002 | Baldwin |
| 2003/0124023 A1 | 7/2003 | Burgess et al. |
| 2004/0008523 A1 | 1/2004 | Butler |
| 2005/0040772 A1 | 2/2005 | Guzman et al. |
| 2005/0055070 A1 | 3/2005 | Jones et al. |
| 2005/0207159 A1 | 9/2005 | Maxik |
| 2006/0022582 A1 | 2/2006 | Radkov |
| 2006/0186377 A1 | 8/2006 | Takahashi et al. |
| 2006/0262545 A1 | 11/2006 | Piepgras et al. |
| 2007/0231188 A1 | 10/2007 | Jung et al. |
| 2008/0008620 A1 | 1/2008 | Alexiadis |
| 2008/0232085 A1 | 9/2008 | Luettgens et al. |
| 2008/0278927 A1 | 11/2008 | Li et al. |
| 2008/0305004 A1 | 12/2008 | Anderson et al. |
| 2009/0002976 A1 | 1/2009 | Schulz |
| 2009/0034236 A1 | 2/2009 | Reuben |
| 2009/0225640 A1 | 9/2009 | Manabe et al. |
| 2009/0231832 A1 | 9/2009 | Zukauskas et al. |
| 2010/0001648 A1 | 1/2010 | De Clercq et al. |
| 2010/0232135 A1 | 9/2010 | Munehiro et al. |
| 2010/0246169 A1 | 9/2010 | Anderson et al. |
| 2012/0281408 A1 | 11/2012 | Owen et al. |
| 2012/0320607 A1 | 12/2012 | Kinomoto et al. |
| 2013/0077299 A1 | 3/2013 | Hussell et al. |
| 2013/0234041 A1 | 9/2013 | Deal |
| 2013/0313516 A1 | 11/2013 | David et al. |
| 2013/0313546 A1 | 11/2013 | Yu |
| 2014/0254131 A1 | 9/2014 | Osinski et al. |
| 2014/0328046 A1 | 11/2014 | Aanegola et al. |
| 2015/0062907 A1 | 3/2015 | Ng et al. |
| 2015/0086420 A1 | 3/2015 | Trapani |
| 2015/0129781 A1 | 5/2015 | Kretschmann |
| 2015/0182646 A1 | 7/2015 | Anderson et al. |
| 2016/0015840 A1 | 1/2016 | Gordon |
| 2016/0030609 A1 | 2/2016 | Peterson et al. |
| 2016/0030610 A1 | 2/2016 | Peterson et al. |
| 2016/0135271 A1 | 5/2016 | Alexander |
| 2016/0271281 A1 | 9/2016 | Clynne et al. |
| 2016/0273717 A1 | 9/2016 | Krames et al. |
| 2016/0276550 A1 | 9/2016 | David et al. |
| 2016/0375161 A1 | 12/2016 | Hawkins et al. |
| 2016/0375162 A1 | 12/2016 | Marry et al. |
| 2016/0375163 A1 | 12/2016 | Hawkins et al. |
| 2017/0014538 A1 | 1/2017 | Rantala |
| 2018/0243452 A1 | 8/2018 | Hawkins et al. |
| 2018/0243453 A1 | 8/2018 | Hawkins et al. |
| 2018/0311386 A1 | 11/2018 | Hawkins et al. |
| 2018/0311387 A1 | 11/2018 | Hawkins et al. |
| 2018/0326104 A1 | 11/2018 | Hawkins et al. |
| 2019/0083667 A1 | 3/2019 | Hawkins et al. |

FOREIGN PATENT DOCUMENTS

| | | |
|---|---|---|
| CN | 201244218 Y | 5/2009 |
| CN | 104421710 A | 3/2015 |
| EP | 1693016 A1 | 8/2006 |
| EP | 1887298 A1 | 2/2008 |
| EP | 1943880 B1 | 4/2013 |
| JP | 2003339845 A | 12/2003 |
| JP | 2008-079510 A | 4/2008 |
| JP | 2010-207278 A | 9/2010 |
| JP | 2014-125692 A | 7/2014 |
| JP | 2014-210922 A | 11/2014 |
| WO | WO-0114012 A1 | 3/2001 |
| WO | WO-03063902 A2 | 8/2003 |
| WO | WO-2004033028 A2 | 4/2004 |
| WO | WO-2006100303 A2 | 9/2006 |
| WO | WO-2006126482 A1 | 11/2006 |
| WO | WO-2007012875 A1 | 2/2007 |
| WO | WO-2009056838 A1 | 5/2009 |
| WO | WO-2015/066099 A2 | 5/2015 |
| WO | WO-2016/019029 A1 | 2/2016 |

OTHER PUBLICATIONS

Australian Patent Application No. 2016283968, Examination Report No. 1, dated Aug. 15, 2018.
Bumah et al., Wavelength and bacterial density influence the bactericidal effect of blue light on methicillin-resistant *Staphylococcus aureus* (MRSA), Photomedicine and Laser Surgery, 31(11): 7 pp. (Nov. 1, 2013 published online).
Edmiston, Air contamination and SSI risk—do we need a new standard?, Session 2207, APIC 2018, Minneapolis, Minnesota (Jun. 14, 2018).
Loftus et al., Methicillin-resistant *Staphylococcus aureus* has a greater risk of transmission in the operating room than methicillin-sensitive *S aureus*, Am. J. Infection Control, 46:520-5 (2018).
Loftus et al., Multiple reservoirs contribute to intraoperative bacterial transmission, Anesth. Analg., 114(6):1236-48 (Jun. 2012).
Loftus et al., The dynamics and implications of bacterial transmission events arising from the anesthesia work area, Anesth. Analg., 120(4):853-60 (Apr. 2015).
Loftus et al., Transmission of pathogenic bacterial organisms in the anesthesia work area, Anesthesiology, 109(3):399-407 (Sep. 2008).
Parvizi et al., Environment of care: Is it time to reassess microbial contamination of the operating room air as a risk factor for surgical site infection in total joint arthroplasty?, Am. J. Infection Control, 45:1267-72 (2017).
Speier et al., Color temperature tunable white light LED system, Proc. SPIE 6337, Sixth International Conference on Solid State Lighting, 63371F (Sep. 12, 2006).
Yezli et al., Surface contamination in operating rooms: a risk for transmission of pathogens?, Surg. Infect. (Larchmt), 15(6):694-9 (Dec. 2014).
Bache et al., "Clinical studies of the High-Intensity Narrow-Spectrum light Environmental Decontamination System (HINS-light EDS), for continuous disinfection in the burn unit inpatient and outpatient settings", Burns, 38(1):69-76 (2012).
Color Phenomena, "CIE-1931 Chromaticity Diagram", 2010, retrieved from www.color-theory-phenomena.nl/10.02.htm on Jun. 7, 2017, 3 pages.
Dai et al., "Blue light for infectious diseases: Propionibacterium acnes, Helicobacter pylori, and beyond?", Drug Resist Updat., 15(4): 223-236 (2012).
Halstead et al., "Antibacterial activity of blue light against nosocomial wound pathogens growing planktonically and as mature biofilms", Appl Environ Microbiol., 82(13):4006-16 (2016).
International Search Report and Written Opinion, International Application No. PCT/GB2008/003679 dated Mar. 3, 2009.

(56) References Cited

OTHER PUBLICATIONS

International Preliminary Report on Patentability, International Application No. PCT/GB2008/003679 dated May 4, 2010.
International Search Report and Written Opinion, International Application No. PCT/US2015/042678 dated Nov. 2, 2015.
International Search Report and Written Opinion, International Application No. PCT/US2016/044634 dated Oct. 20, 2016.
McDonald et al., "405 nm Light exposure of osteoblasts and inactivation of bacterial isolates from arthroplasty patients: potential for new disinfection applications?", European Cells and Materials, 25:204-14 (2013).
Tomb et al., " Inactivation of Streptomyces phage ?C31 by 405 nm light", Bacteriophage, 4:e32129-1-6 (2014).
Tsukada et al., "Bactericidal action of photo-irradiated aqueous extracts from the residue of crushed grapes from winemaking", Biocontrol Science, 21(2): 113-121 (2016).
LEDs Magazine, "Lumination Vio LED combines 405 nm chip with new phosphors". Retrieved from the Internet on Aug. 2, 2016 at: <URL:<http://www.ledsmagazine.com/articles/2007/06/lumination-vio-led-combines-405-nm-chip-with-new-phosphors.html>.
LEDs Magazine, "ANSI evaluates revisions to SSL chromaticity standard". Retrieved from the Internet on Aug. 2, 2016 at: <URL:<http://www.ledsmagazine.com/articles/2011/07/ansi-evaluates-revisions-to-ssl-chromaticity-standard-magazine.html> (2011).
LEDs Magazine, "ANSI works to update the solid-state lighting standard for chromaticity". Retrieved from the Internet on Aug. 2, 2016 at: <URL:<http://www.ledsmagazine.com/articles/print/volume-12/issue-2/features/standards/ansi-works-to-update-the-ssl-chromaticity-standard.html> (2015).
LEDs Magazine, "ANSI continues advancements on SSL chromaticity standard". Retrieved from the Internet on Aug. 2, 2016 at: <URL:<http://www.ledsmagazine.com/articles/print/volume-12/issue-11/features/standards/ansi-continues-advancements-on-ssl-chromaticity-standard.html> (2015).
SORAA, "PAR30L". Retrieved from the Internet on Aug. 2, 2016 at: <URL:<http://www.soraa.com/products/22-PAR30L>.
SORRA, "PAR3OL 18.5W", Retrieved from the Internet on Aug. 2, 2016 at: <URL:http://www.soraa.com/products.
International Search Report for Application No. PCT/US2016/036704 dated Dec. 8, 2016.
Written Opinion for Application No. PCT/US2016/036704 dated Dec. 8, 2016.
Written Opinion for Application No. PCT/US2016/036704 dated May 29, 2017.
U.S. Appl. No. 15/178,461, filed Jun. 9, 2016, Patrick J. Marry et al.
U.S. Appl. No. 15/178,463, filed Jun. 9, 2016, James W. Hawkins et al.
Guffey et al., In vitro bactericidal effects of 405-nm and 470-nm blue light, Photomedicine and Laser Surgery, 24(6):684-8 (2006).
Japanese patent application No. 2018-519679, Office Action, dated Apr. 23, 2019.
Chinese Patent Application No. 201680037376.7, First Office Action, dated May 17, 2019.

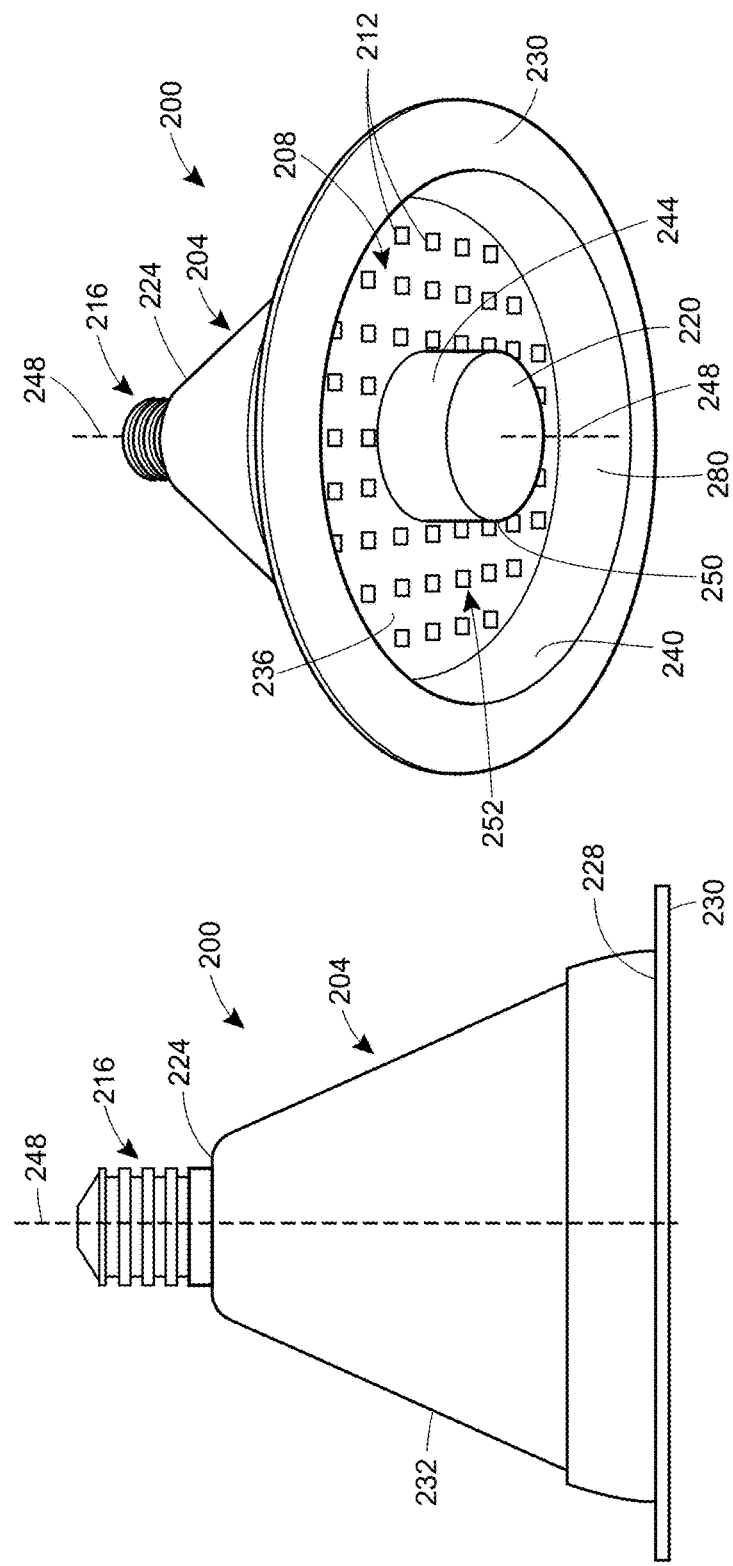

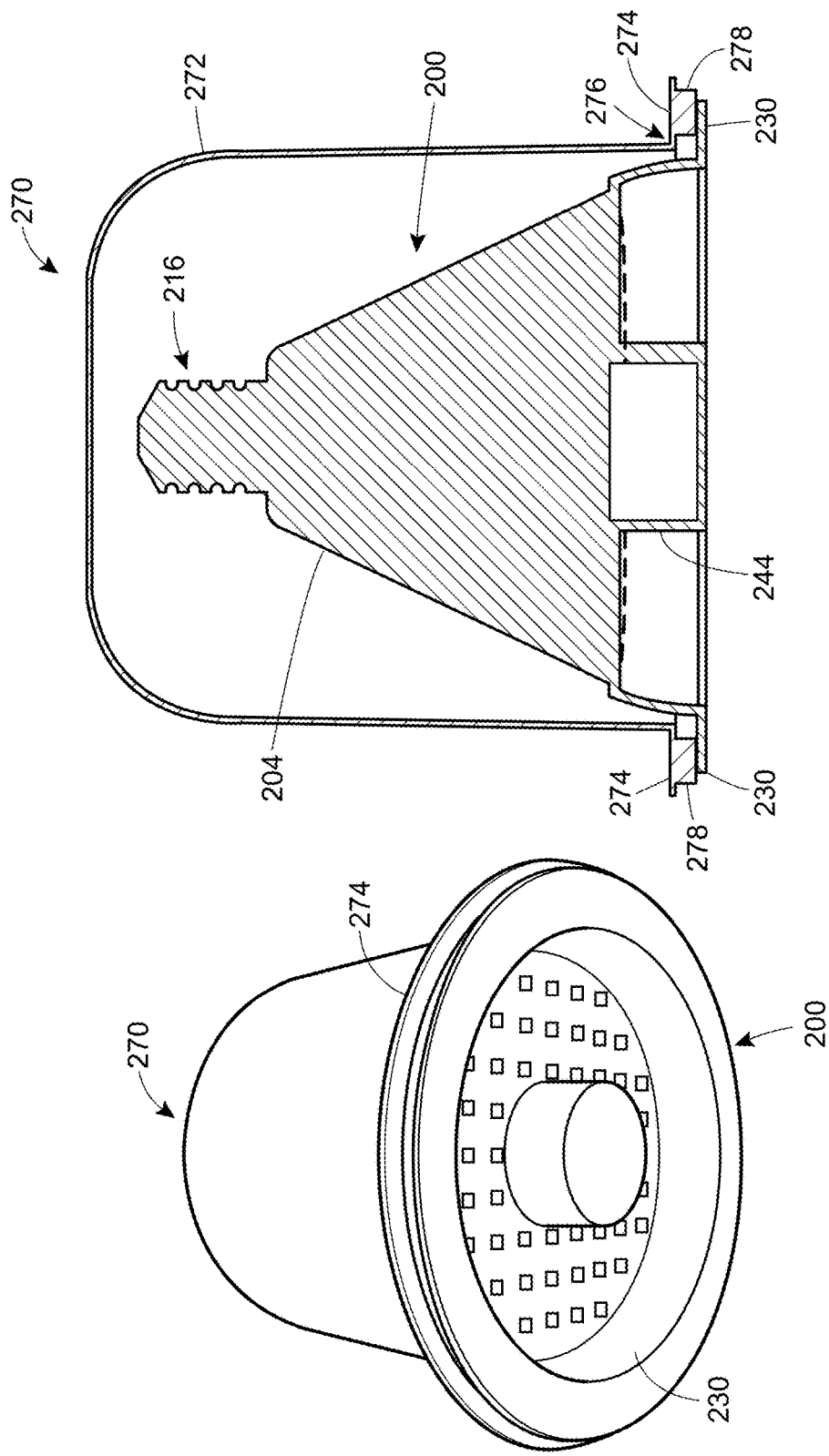

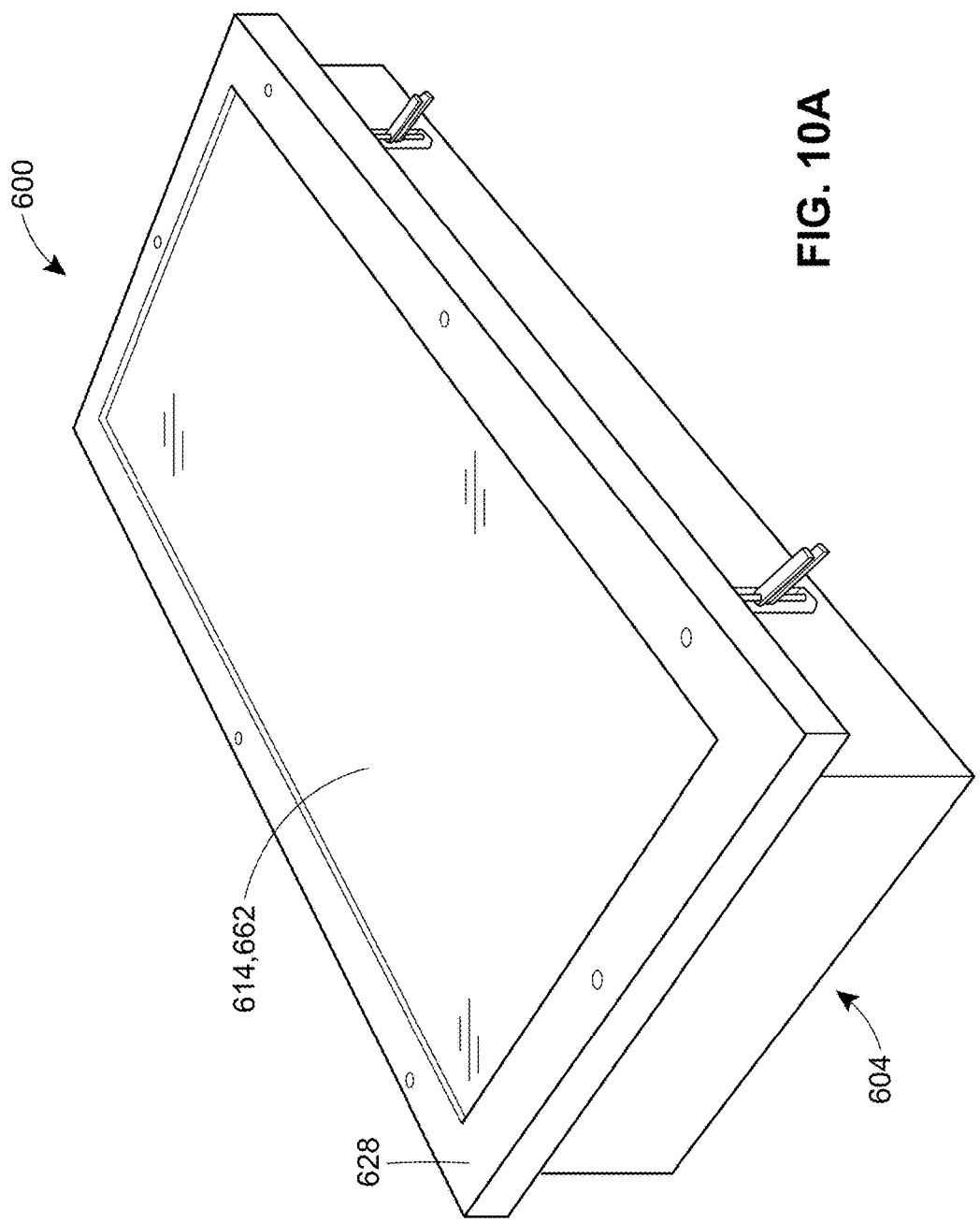

| ZONAL LUMEN SUMMARY ||
| Zone | Lumens |
| --- | --- |
| 0-10 | 493.41 |
| 10-20 | 1397.87 |
| 20-30 | 2063.47 |
| 30-40 | 2376.24 |
| 40-50 | 2308.35 |
| 50-60 | 1930.14 |
| 60-70 | 1363.09 |
| 70-80 | 736.54 |
| 80-90 | 204.74 |
| 90-100 | 4.97 |
| 100-110 | 3.52 |
| 110-120 | 3.27 |
| 120-130 | 2.79 |
| 130-140 | 3.33 |
| 140-150 | 6.52 |
| 150-160 | 16.26 |
| 160-170 | 18.35 |
| 170-180 | 5.00 |

FIG. 11F

| ZONAL LUMEN SUMMARY ||
| Zone | Lumens |
| --- | --- |
| 0-10 | 111.70 |
| 10-20 | 359.12 |
| 20-30 | 614.39 |
| 30-40 | 756.65 |
| 40-50 | 691.23 |
| 50-60 | 496.87 |
| 60-70 | 294.40 |
| 70-80 | 121.30 |
| 80-90 | 19.16 |
| 90-100 | 0.00 |
| 100-110 | 0.00 |
| 110-120 | 0.00 |
| 120-130 | 0.00 |
| 130-140 | 0.00 |
| 140-150 | 0.00 |
| 150-160 | 0.00 |
| 160-170 | 0.00 |
| 170-180 | 0.00 |

FIG. 11G

| ZONAL LUMEN SUMMARY ||
| Zone | Lumens |
| --- | --- |
| 0-10 | 202.56 |
| 10-20 | 698.13 |
| 20-30 | 1055.48 |
| 30-40 | 866.24 |
| 40-50 | 281.54 |
| 50-60 | 41.20 |
| 60-70 | 7.46 |
| 70-80 | 2.55 |
| 80-90 | 0.50 |
| 90-100 | 0.00 |
| 100-110 | 0.01 |
| 110-120 | 0.02 |
| 120-130 | 0.02 |
| 130-140 | 0.06 |
| 140-150 | 0.35 |
| 150-160 | 0.86 |
| 160-170 | 2.19 |
| 170-180 | 1.92 |

FIG. 11H

| ZONAL LUMEN SUMMARY ||
| Zone | Lumens |
| --- | --- |
| 0-10 | 37.06 |
| 10-20 | 107.39 |
| 20-30 | 166.10 |
| 30-40 | 204.06 |
| 40-50 | 215.31 |
| 50-60 | 198.40 |
| 60-70 | 155.79 |
| 70-80 | 96.36 |
| 80-90 | 31.81 |
| 90-100 | 312.71 |
| 100-110 | 920.14 |
| 110-120 | 943.09 |
| 120-130 | 853.05 |
| 130-140 | 715.12 |
| 140-150 | 545.07 |
| 150-160 | 362.11 |
| 160-170 | 190.90 |
| 170-180 | 56.95 |

FIG. 11I

SINGLE-EMITTER LIGHTING DEVICE THAT OUTPUTS A MINIMUM AMOUNT OF POWER TO PRODUCE INTEGRATED RADIANCE VALUES SUFFICIENT FOR DEACTIVATING PATHOGENS

CROSS-REFERENCE TO RELATED APPLICATIONS

This application is a continuation of U.S. patent application Ser. No. 15/178,349, entitled "Single-Emitter Lighting Device that Outputs a Minimum Amount of Power to Produce Integrated Radiance Values Sufficient for Deactivating Pathogens," and filed on Jun. 9, 2016, which claims the benefit of U.S. Provisional Patent Application No. 62/185,391, entitled "Lamp or Fixture Enclosure for Delivering Radiation," and filed on Jun. 26, 2015 and U.S. Provisional Patent Application No. 62/190,113, entitled "Lighting Device for Deactivating Pathogens," and filed on Jul. 8, 2015, the entire disclosures of which are hereby incorporated by reference herein.

FIELD

The present disclosure generally relates to lighting devices and, more particularly, to a single-emitter lighting device that outputs a minimum amount of power for deactivating pathogens.

BACKGROUND

Pathogens, such as viruses, bacteria, and fungi, are responsible for numerous diseases or infections, including some very dangerous and potentially fatal diseases and infections, that affect humans, animals, and plants. Environments, such as health-care environments (e.g., hospitals) and restaurants, are particularly susceptible to the transmission or spread of such pathogens. Indeed, healthcare associated infections (HAIs), which are caused by pathogens, such as Mehicillin-resistant *Staphylococcus aureus* (MRSA), *Closridium difficile* (*C. difficile*), transmitted through, for example, person-to-person contact and skin shedding in healthcare environments, are an increasingly dangerous problem for the healthcare industry. According to the Center for Disease Control and Prevention, HAIs cause at least 1.7 million illnesses and 99,000 deaths in acute care hospitals in the U.S. alone every year. Pathogens can also serve to spoil food products (e.g., fruits, vegetables) and result in the loss of goods and raw materials in various industrial processes, for example chemical processing, brewing and distillation, food packaging, and other processes that require non-contaminated environments.

Significant resources have already been committed to preventing and controlling pathogens in these environments, but to this point, these resources have not yielded the desired results. Some existing methods of pathogen control, e.g., those involving hygiene, have proven to be labor-intensive, difficult to monitor, and, most importantly, of limited effectiveness (e.g., are only temporarily effective, only deactivate some pathogens). Other known methods of pathogen control, e.g., those involving UV-light, ozone and chemical fumigation, while successful, are toxic to humans. Thus, environments requiring decontamination must be sealed off and cannot be used during the process.

SUMMARY

One aspect of the present disclosure provides a lighting device configured to deactivate dangerous pathogens (e.g., MRSA bacteria) in an environment. The lighting device includes at least one lighting element with a single light source configured to provide light. At least a first component of the light comprising light having a wavelength of about 405 nm, and at least a second component of the light comprising light having a wavelength of greater than 420 nm. The first component of light has a minimum integrated irradiance of 0.01 mW/cm$^2$ measured from any unshielded point in the environment that is 1.5 m from any point on any external-most luminous surface of the lighting device.

Another aspect of the present disclosure provides a lighting device configured to deactivate dangerous pathogens (e.g., MRSA bacteria) in an environment. The lighting device includes at least one light-emitting element configured to emit light having a wavelength of about 405 nm, and at least one light converting element. At least a first component of the light emitted by the at least one light-emitting element travels through the at least one light converting element without alteration, and at least a second component of the light emitted by the at least one light-emitting element is converted into light having a wavelength of greater than 420 nm. The first component of the light has a minimum integrated irradiance of 0.01 mW/cm$^2$ measured from any unshielded point in the environment that is 1.5 m from any point on any external-most luminous surface of the lighting device.

Another aspect of the present disclosure provides a method of deactivating dangerous pathogens (e.g., MRSA bacteria) in an environment. The method includes providing light from at least one lighting element of a lighting device installed in the environment. At least a first component of the light has a wavelength of about 405 nm and has a minimum integrated irradiance of 0.01 mW/cm$^2$ measured from any unshielded point in the environment that is 1.5 m from any point on any external-most luminous surface of the lighting device, and at least a second component of the light has a wavelength of greater than 420 nm.

BRIEF DESCRIPTION OF THE DRAWINGS

The accompanying figures, where like reference numerals refer to identical or functionally similar elements throughout the separate views, together with the detailed description below, are incorporated in and form part of the specification, and serve to further illustrate embodiments of concepts that include the claimed embodiments, and explain various principles and advantages of those embodiments.

FIG. 4A is a plan view of one exemplary version of the lighting device of FIG. 2.

FIG. 4B is a rear perspective view of the lighting device of FIG. 4A.

FIG. 5A is a perspective view of the lighting device of FIGS. 4A-4D installed in a receiving structure of the environment.

FIG. 5B is a cross-sectional view of FIG. 5A.

FIG. 10A is a perspective view of another exemplary version of the lighting device of FIG. 2.

FIG. 11F depicts a chart of luminous flux for the light distribution plot of FIG. 11B;

FIG. 11G depicts a chart of luminous flux for the light distribution plot of FIG. 11C;

FIG. 11H depicts a chart of luminous flux for the light distribution plot of FIG. 11D;

FIG. 11I depicts a chart of luminous flux for the light distribution plot of FIG. 11E;

DETAILED DESCRIPTION

Figure 1:
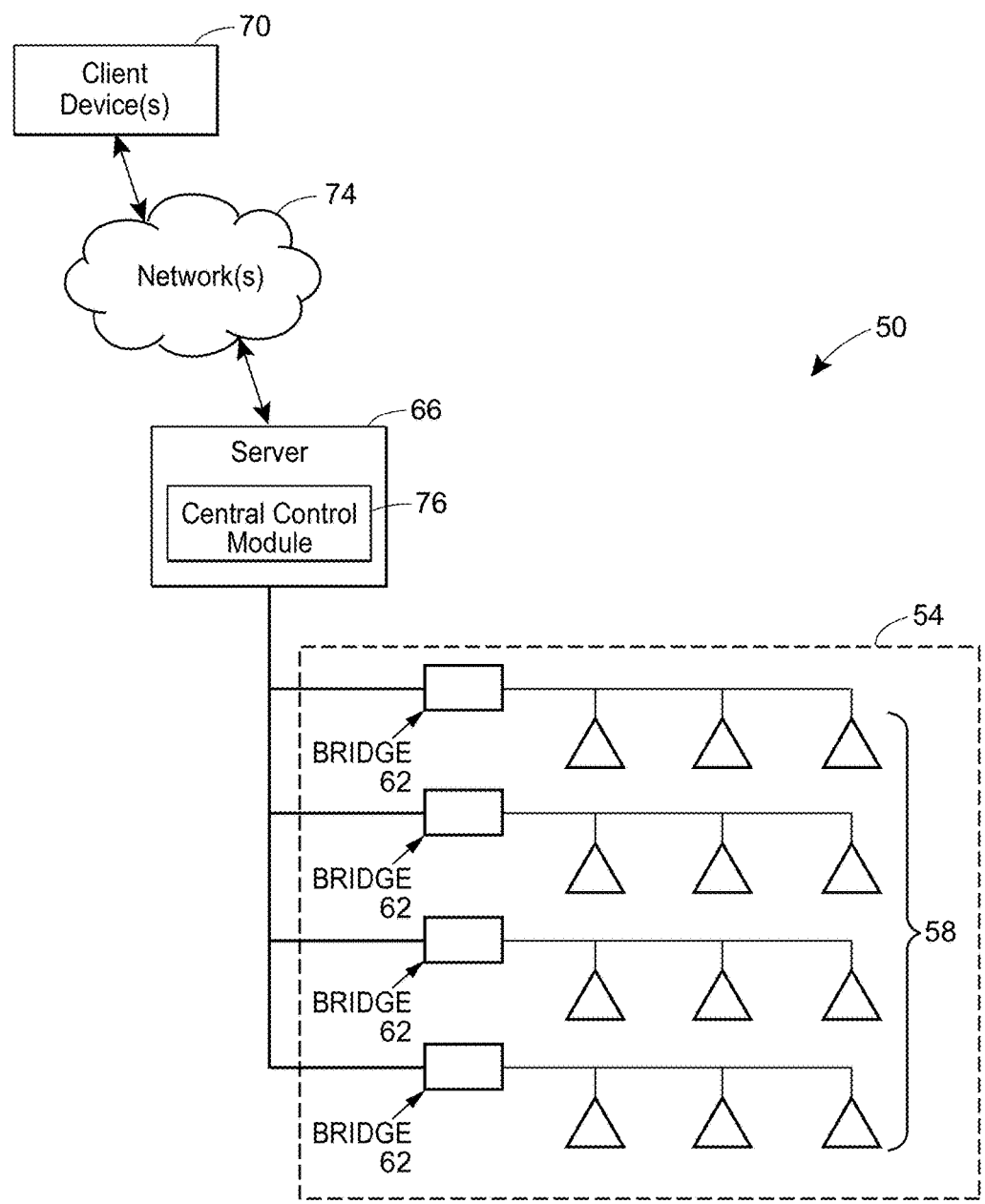
FIG. 1 is a schematic diagram of a lighting system constructed in accordance with the teachings of the present disclosure and employed in an environment susceptible to the transmission of pathogens.

FIG. 1 depicts a lighting system 50 that may be implemented or included in an environment 54, such as, for example, a hospital, a doctor's office, an examination room, a laboratory, a nursing home, a health club, a retail store (e.g., grocery store), a restaurant, or other space or building, or portions thereof, where it is desirable to both provide illumination and to reduce, and ideally eliminate, the existence and spread of the pathogens described above.

The lighting system 50 illustrated in FIG. 1 generally includes a plurality of lighting devices 58, a plurality of bridge devices 62, a server 66, and one or more client devices 70 configured to connect to the server 66 via one or more networks 74. Of course, if desired, the lighting system 50 can include more or less components and/or different components. For example, the lighting system 50 need not necessarily include bridge devices 62 and/or client devices 70.

Each of the lighting devices 58 is installed in or at the environment 54 and includes one or more light-emitting components, such as light-emitting diodes (LEDs), fluorescent lamps, incandescent bulbs, laser diodes, or plasma lights, that, when powered, (i) illuminate an area of the environment 54 proximate to or in vicinity of the respective lighting device 58, and (ii) deliver sufficient doses of visible light to deactivate pathogens in the illuminated area, as will be described below. In one version, the lighting devices 58 can be uniformly constructed. In another version, the lighting devices 58 can vary in type, shape, and/or size. As an example, the lighting system 50 can employ various combinations of the different lighting devices described herein.

The bridge devices 62 are, at least in this example, located at the environment 54 and are communicatively connected (e.g., via wired and/or wireless connections) to one or more of the lighting devices 58. In the lighting system 50 illustrated in FIG. 1, four bridge devices 62 are utilized, with each bridge device 62 connected to three different lighting devices 58. In other examples, more or less bridge devices 62 can be connected to more or less lighting devices 58.

The server 66 may be any type of server, such as, for example, an application server, a database server, a file server, a web server, or other server). The server 66 may include one or more computers and/or may be part of a larger network of servers. The server 66 is communicatively connected (e.g., via wired and/or wireless connections) to the bridge devices 62. The server 66 can be located remotely (e.g., in the "cloud") from the lighting devices 58 and the client devices 70 and may include one or more processors, controller modules (e.g., a central controller 76), or the like that are configured to facilitate various communications and commands among the client devices 70, the bridge devices 62, and the lighting devices 58. As such, the server 66 can generate and send commands or instructions to the lighting devices 58 to implement various sets of lighting settings corresponding to operation of the lighting devices 58. Each set of lighting settings may include various parameters or settings including, for example, spectral characteristics, operating modes (e.g., examination mode, disinfection mode, blended mode, nighttime mode, daytime mode, etc.), dim levels, output wattages, intensities, timeouts, and/or the like, whereby each set of lighting settings may also include a schedule or table specifying which settings should be used based on the time of day, day or week, natural light levels, occupancy, and/or other parameters. The server 66 can also receive and monitor data, such as operating status, light emission data (e.g., what and when light was emitted), hardware information, occupancy data, daylight levels, temperature, power consumption, and dosing data, from the lighting devices 58 via the bridge devices 62. In some cases, this data can be recorded and used to form or generate reports, e.g., a report indicative of the characteristics of the light emitted by one or more of the lighting devices 58. Such reports may, for example, be useful in evidencing that the environment 54 was, at or during various periods of time, delivering sufficient doses of visible light to deactivate pathogens in the illuminated area.

The network(s) 74 may be any type of wired, wireless, or wireless and wired network, such as, for example, a wide area network (WAN), a local area network (LAN), a personal area network (PAN), or other network. The network(s) 74 can facilitate any type of data communication via any standard or technology (e.g., GSM, CDMA, TDMA, WCDMA, LTE, EDGE, OFDM, GPRS, EV-DO, UWB, IEEE 802 including Ethernet, WiMAX, WiFi, Bluetooth®, and others).

The client device(s) 70 may be any type of electronic device, such as a smartphone, a desktop computer, a laptop, a tablet, a phablet, a smart watch, smart glasses, wearable electronics, a pager, a personal digital assistant, or any other electronic device, including computing devices configured for wireless radio frequency (RF) communication. The client device(s) 70 may support a graphical user interface (GUI), whereby a user of the client device(s) 70 may use the GUI to select various operations, change settings, view operation statuses and reports, make updates, configure email/text alert notifications, and/or perform other functions. The client device(s) 70 may transmit, via the network(s) 74, the server 66, and the bridge device(s) 62, any updated light settings to the lighting devices 58 for implementation and/or storage thereon. The client device(s) 70 may facilitate data communications via a gateway access point that may be connected to the bridge device(s) 62. In one implementation, the gateway access point may be a cellular access point that includes a gateway, an industrial Ethernet switch, and a cellular router integrated into a sealed enclosure. Further, the gateway access point may be secured using HTTPS with a self-signed certificate for access to web services, and may push/pull data between various websites, the one or more bridge devices 62, and the lighting devices 58.

Figure 2:
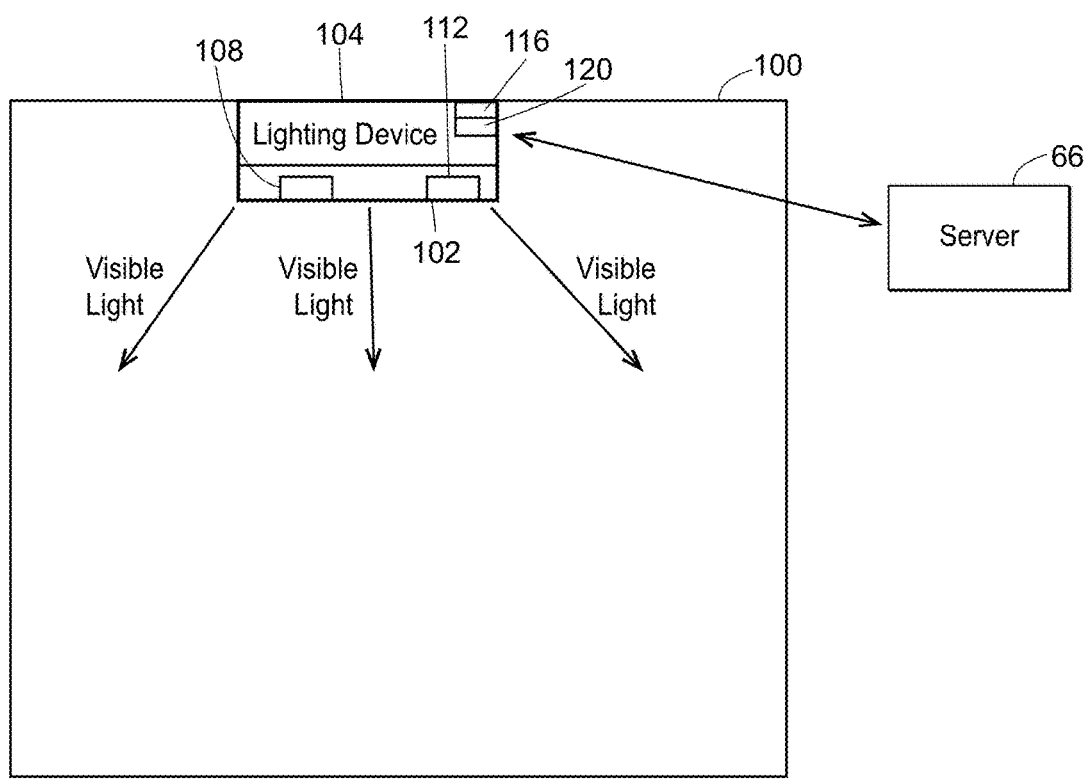
FIG. 2 is a schematic of a portion of the environment of FIG. 1 including a lighting device constructed in accordance with the teachings of the present disclosure, the lighting device configured to deactivate pathogens in that portion of the environment.

FIG. 2 illustrates a healthcare environment 100 that includes one of the lighting devices 58, taking the form of a lighting device 104 constructed in accordance with the present disclosure. The healthcare environment 100, which can, for example, be or include an examination room, an operating room, a bathroom, a hallway, a waiting room, a closet or other storage area, a Clean room, or a portion thereof, is generally susceptible to the spread of dangerous pathogens, as discussed above.

Laboratory studies have shown that specially configured doses of narrow spectrum visible light (e.g., light having a wavelength between 400 nm and 420 nm) can, when delivered at sufficiently high power levels (e.g., above 3,000 mW), effectively deactivate (or destroy) dangerous pathogens. However, these doses tend to have a distracting or objectionable aesthetic impact in or upon the environment to which they are delivered. For example, these doses may provide an output of light that is undesirable when performing surgery in the healthcare environment 100. Thus, it has proven difficult to incorporate these doses into lighting devices that can simultaneously deactivate pathogens and illuminate an environment (e.g., the healthcare environment 100) in a non-objectionable manner. Instead, doses of narrow spectrum visible light are typically only delivered in when the environment is unoccupied, thereby severely limiting the deactivation potential of such lighting devices.

The lighting device 104 described herein is configured to deliver doses of narrow spectrum visible light at power levels sufficiently high enough to effectively deactivate dangerous pathogens in the healthcare environment 100 (or other environment), and, at the same time, provide visible light that sufficiently illuminates the environment 100 (or other environment) in a safe and unobjectionable manner.

More specifically, the lighting device 104 provides or delivers (e.g., outputs, emits) at least 3,000 mW (or 3 W) of disinfecting light, which has a wavelength in the range of approximately 380 nm to approximately 420 nm, and more particularly between 400 nm and 420 nm, to the environment 100, as it will be appreciated that doses of light having a wavelength in this range but delivered at power levels lower than 3,000 mW are generally ineffective in deactivating dangerous pathogens. The lighting device 104 may, for example, provide or deliver 3,000 mW, 4,000 mW (or 4 W), 5,000 mW (or 5 W), 6,000 mW (or 6 W), 7,000 mW (or 7 W), 10,500 mW (or 10.5 W), or some other level of disinfecting light above 3,000 mW. The lighting device 104 also provides or delivers levels of disinfecting light such that any exposed surface within the environment 100 has or achieves a desired, minimum power density while the lighting device 104 is used for deactivation, thereby ensuring that the environment 100 is adequately disinfected. This desired, minimum power density is the minimum power, measured in mW, received by any exposed surface per unit area, measured in $cm^2$. When measured or determined over time (the period of time over which the lighting device 104 is used for deactivation), this minimum power density within the applicable bandwidth of visible light may be referred to, as it is herein, as the minimum integrated irradiance, measured in $mW/cm^2$. The minimum integrated irradiance of the disinfecting light provided by the lighting device 104, which in this example is measured from any exposed surface or unshielded point in the environment 100 that is 1.5 m from any point on any external-most luminous surface 102 of the lighting device 104 but may in other examples be measured from a different distance from any external-most luminous surface 102, nadir, any unshielded point in the environment 100, or some other point, is generally equal to at least 0.01 mW/cm2. The minimum integrated irradiance may, for example, be equal to 0.02 $mW/cm^2$, 0.05 $mW/cm^2$, 0.1 $mW/cm^2$, 0.15 $mW/cm^2$, 0.20 $mW/cm^2$, 0.25 $mW/cm^2$, 0.30 $mW/cm^2$, or some other value greater than 0.01 $mW/cm^2$.

At the same time, the lighting device 104 provides an output of visible light that is perceived by humans (e.g., patients, personnel) in and around the environment 100 as white light, with properties that studies have shown to be aesthetically pleasing, or at least unobjectionable, to humans, and has a disinfection component including narrow spectrum visible light. While the exact properties of the white light may vary depending on the given application, the properties generally include one or more of the following: (1) a desirable color rendering index, e.g., a color rendering index of greater than 70, greater than 80, or greater than 90; (2) a desirable color temperature, e.g., a color temperature of between approximately 1500 degrees Kelvin and 7000 degrees Kelvin, more particularly between approximately 1800 degrees and 5000 degrees Kelvin, between approximately 2100 degrees and 6000 degrees Kelvin, between approximately 2700 degrees and 5000 degrees Kelvin, or some other temperature or range of temperatures within these ranges or partially or totally outside of these ranges; or (3) a desirable chromaticity.

Figure 3A:
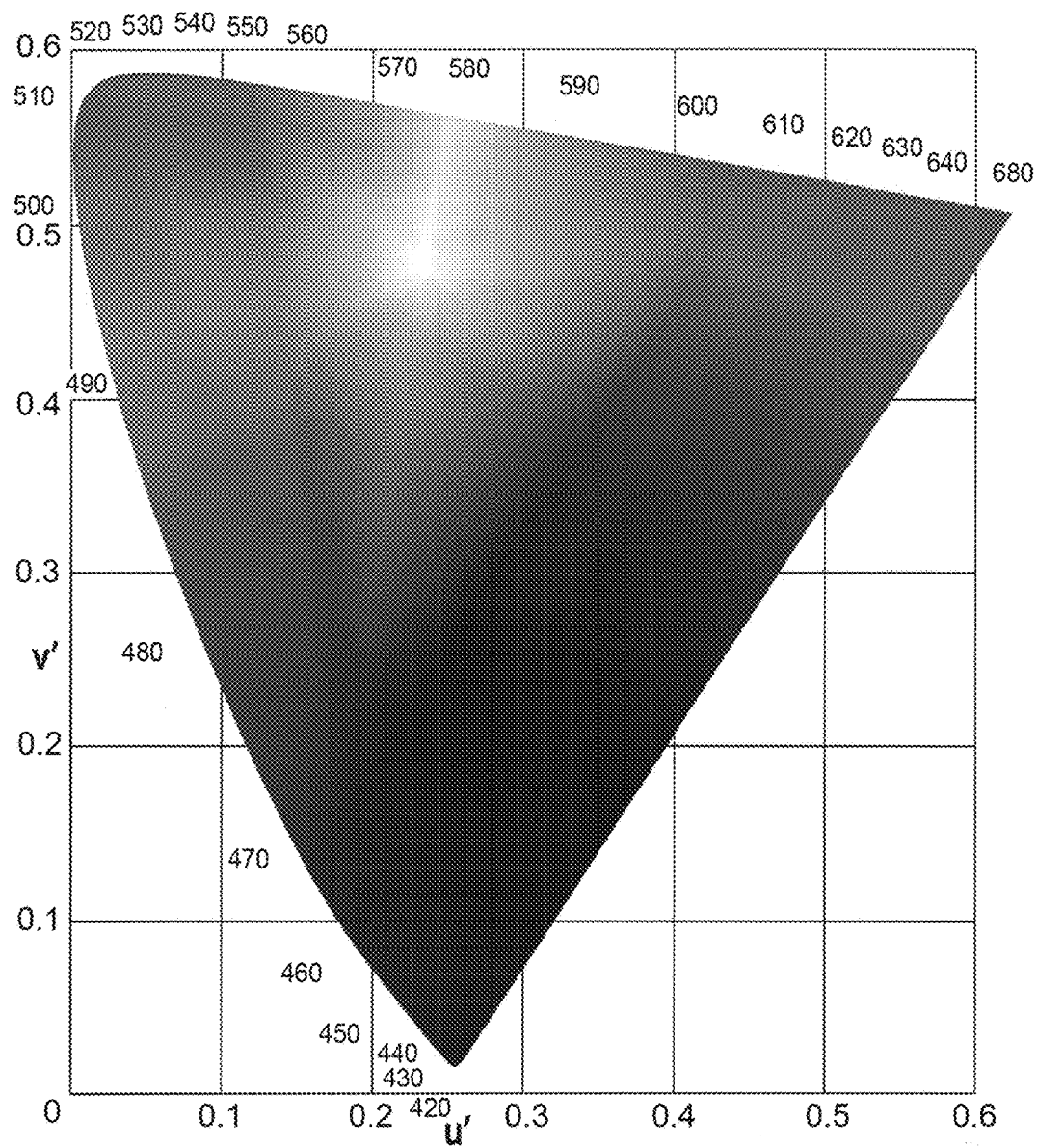
FIG. 3A illustrates the CIE 1976 chromaticity diagram.
Figure 3B:
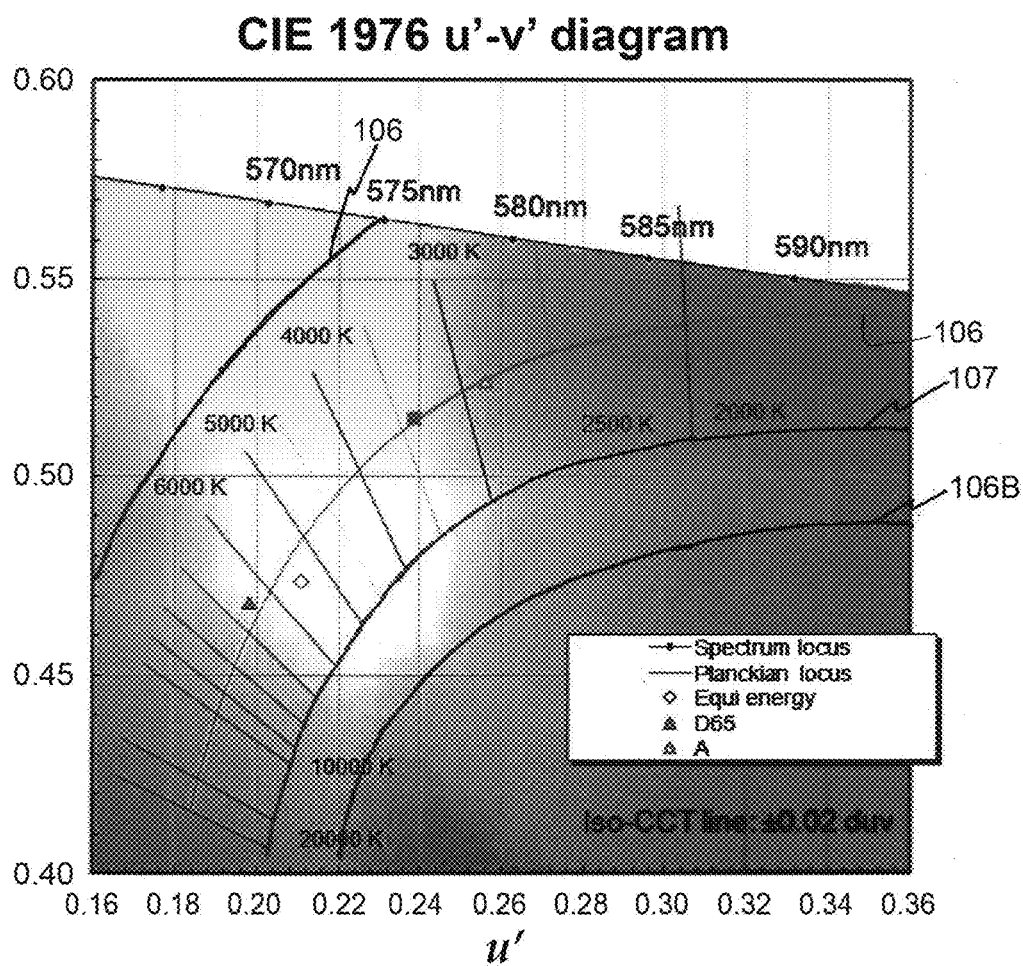
FIG. 3B is a close-up, partial view of the diagram of FIG. 3A, showing a range of curves of white visible light that can be output by the lighting device of FIG. 2 such that the lighting device can provide visually appealing, unobjectionable white light.

Chromaticity can be described relative to any number of different chromaticity diagrams, such as, for example, the 1931 CIE Chromaticity Diagram, the 1960 CIE Chromaticity Diagram, or the 1976 CIE Chromaticity Diagram shown in FIG. 3A. The aesthetically pleasing white light output by the lighting device 104 can thus be described as having properties relative to or based on these chromaticity diagrams. As illustrated in, for example, FIG. 3B, the white light output by the lighting device 104 may have u', v' coordinates on the 1976 CIE Chromaticity Diagram (FIG. 3A) that lie on any number of different curves relative to a planckian locus 105 defined by the ANSI C78.377-2015 color standard. The ANSI C78.377-2015 color standard generally describes the range of color mixing that creates pleasing, or visually appealing, white light. This range is generally defined by the planckian locus 105, which is also known as a blackbody curve, with some deviation, measured in Duv, above or below the planckian locus 105. The different curves on which the u', v' coordinates of the white light output can lie deviate from the planckian locus 106 by different Duv values, depending upon the given application. The white light may, for example, lie on a curve 106A that is 0.035 Duv above the planckian locus 105, on a curve 106B that is 0.035 Duv below (−0.035 Duv) the planckian locus 105, on a curve 107 that is 0.02 Duv below (−0.02 Duv) the planckian locus 105, on a curve that is 0.02 Duv above the planckian locus, or some other curve between 0.035 Duv above and 0.035 Duv below the planckian locus 105.

The lighting device 104 is, in some cases, fully enclosed, which promotes cleanliness, by, for example, preventing pathogens from nesting on or within internal components of the lighting device 104, which would otherwise be hard to reach with the specially configured narrow spectrum visible light. In other words, in these cases, no surface internal to the lighting device 104 is exposed to the environment 100 surrounding the lighting device 104, such that dangerous pathogens cannot reside on surfaces hidden from the narrow spectrum visible light.

As will be described herein, the lighting device 104 includes one or more light-emitting elements, e.g., light-emitting diodes (LEDs), configured to emit light as desired. The lighting device 104 optionally includes one or more reflectors, one or more lenses, one or more diffusers, and/or one or more other components. In some examples, e.g., when LEDs are employed in the lighting device, the lighting device 104 can include a means for maintaining a junction temperature of the LEDs below a maximum operating temperature of the LEDs. The means for maintaining a junction temperature may, for example, include one or more heat sinks, spreading heat to printed circuit boards coupled to the LEDs, a constant-current driver topology, a thermal feedback system to one or more drivers (that power the LEDs) via NTC thermistor, or other means that reduce LED drive current at sensed elevated temperatures. The lighting device 104 can further include an occupancy sensor 108, a daylight sensor 112, one or more communication modules 116, and one or more control components 120, e.g., a local controller. The lighting device 104 can optionally include one or more additional sensors, e.g., two occupancy sensors 108, a sensor that measures the light output by the device 104, etc.

In this version, the occupancy sensor 108 is an infrared (IR) motion sensor that detects motion within a pre-determined range of or distance from (e.g., 50 feet) the lighting device 104, so as to identify (or help identify) whether the environment 100 is occupied or is vacant (i.e., not occupied) and has been occupied or vacant for a period of time (e.g., a predetermined period of time, such as 15 minutes, 30 minutes, etc.). The occupancy sensor 108 may continuously monitor the environment 100 to determine whether the environment 100 is occupied. In other versions, the occupancy sensor 108 can be a different type of sensor, e.g., an ultrasonic sensor, a microwave sensor, a $CO_2$ sensor, a thermal imaging sensor, that utilizes a different occupancy detection technique or technology to identify (or help identify) whether the environment 100 is or is not occupied and has or has not been occupied for a period of time. In some versions, multiple occupancy sensors 108 that detect occupancy using different detection techniques or technologies can be employed to provide for a more robust detection. As an example, the lighting device 104 can include one infrared motion sensor and one CO2 sensor, which utilize different techniques or technologies to detect occupancy. The daylight sensor 112, meanwhile, is configured to detect natural light within a pre-determined range of or distance from (e.g., 50 feet) the lighting device 104, so as to identify whether it is daytime or nighttime (and thus, whether the environment 100 is or is not occupied).

The lighting device 104 can, responsive to occupancy data obtained by the occupancy sensor 108 and/or natural light data obtained by the daylight sensor 112, be controlled by the local controller 120 (or other control components) to emit visible light of or having various characteristics. The lighting device 104 can, for example, responsive to data indicating that the environment 100 is vacant (i.e., not occupied), be controlled so as to output visible light consisting only of the specially configured narrow spectrum visible light. In some cases, the narrow spectrum visible light is only output after the lighting device 104 determines that the environment 100 has been vacant for a pre-determined period of time (e.g., 30 minutes), thereby providing a fail-safe that ensures that the environment 100 is indeed vacant. The lighting device 104 can, via the communication module(s) 116, be communicatively connected to and controlled by the remotely located server 66 (as well as remotely located client devices 70) and/or be communicatively connected to other lighting devices 58. As such, the lighting device 104 may transmit data, such as operating status (e.g., the operating mode), light emission data, hardware information, occupancy data, daylight levels, output wattages, temperature, power consumption, to the server 66 and/or other lighting devices 58, and may receive, from the server 66, other lighting devices 58, and/or the client devices 70, operational instructions (e.g., turn on, turn off, provide light of a different spectral characteristic, switch between operating modes) and/or other data (e.g., operational data from or about the other lighting devices 58).

It will be appreciated that the lighting device 104 can be manually controlled (e.g., by a user of the lighting device 104) and/or automatically controlled responsive to other settings, parameters, or data in place of or in addition to the data obtained by the occupancy sensor 108 and/or the daylight sensor 112. The lighting device 104 may, for example, be partially or entirely controlled by the local controller 120 (or other control components) responsive to an operating mode, a dim level, a schedule or a table, or other parameter(s) or setting(s) received by the local controller 120 (or other control component(s)).

In some versions, such as the one illustrated in FIG. 2, the lighting device 104 can include a dosing or deactivation feedback system 124 that monitors and records the amount and frequency of dosing delivered by the lighting device 104. The dosing feedback system 124 is, in this version, implemented by the local controller 120, though the dosing feedback system 124 can be implemented using other components (e.g., a suitable processor and memory) in the lighting device 104 or can be implemented via the server 66. In any event, the dosing feedback system 124 achieves the aforementioned aims by monitoring and recording the various parameters or settings of and associated with the lighting device 104 over a period of time. More specifically, the dosing feedback system 124 monitors and records the spectral characteristics, the output wattages, wavelengths, and/or intensities of the light (or components thereof) emitted by the lighting device 104, the minimum integrated irradiance of the disinfecting narrow spectrum visible light provided by the lighting device 104, occupancy data obtained by the occupancy sensor 108, the amount of time the lighting device 104 has spent in various operating modes (e.g., examination mode), dim levels, and the like. As an example, the dosing feedback system 124 monitors and records when the lighting device 104 emits visible light that includes or solely consists of disinfecting narrow spectrum visible light (i.e., light having a wavelength between 400 nm and 420 nm), as well as the levels and density (and more particularly the minimum integrated irradiance) of disinfecting narrow spectrum visible light delivered during those times. Based on the parameters or settings of the lighting device 104, the dosing feedback system 124 (and/or an operator of the lighting device 104) can determine the quantity and frequency of deactivation dosing delivered by the lighting device 104. Alternatively or additionally, the dosing feedback system 124 can provide the recorded data to the server 66 (via the communication module(s) 116), which can in turn determine the quantity and frequency of deactivation dosing delivered by the lighting device 104. In some cases, the dosing feedback system 124 and/or the server 66 can generate periodic reports including the obtained data and/or determinations with respect to deactivation dosing. When the dosing feedback system 124 generates these reports, the reports can be transmitted to the server 66 or any other component via the communication module(s) 116. In any case, the dosing feedback system 124 allows a hospital or other environment 100 that implements the lighting device 104 to quantitatively determine (and verify) that sufficient levels of deactivation dosing were delivered over various periods of time or at certain points in time (e.g., during a particular operation). This can, for example, be extremely beneficial in the event that the hospital or other environment 100 is sued by a patient alleging that she/he acquired a HAI while at the hospital or other environment 100.

Figure 4D:
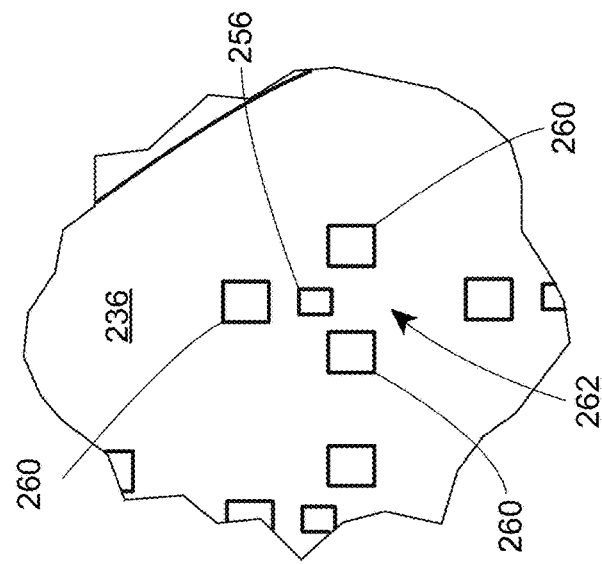
FIG. 4D is a partial, close-up view of a portion of the lighting device of FIG. 4C.
Figure 4C:
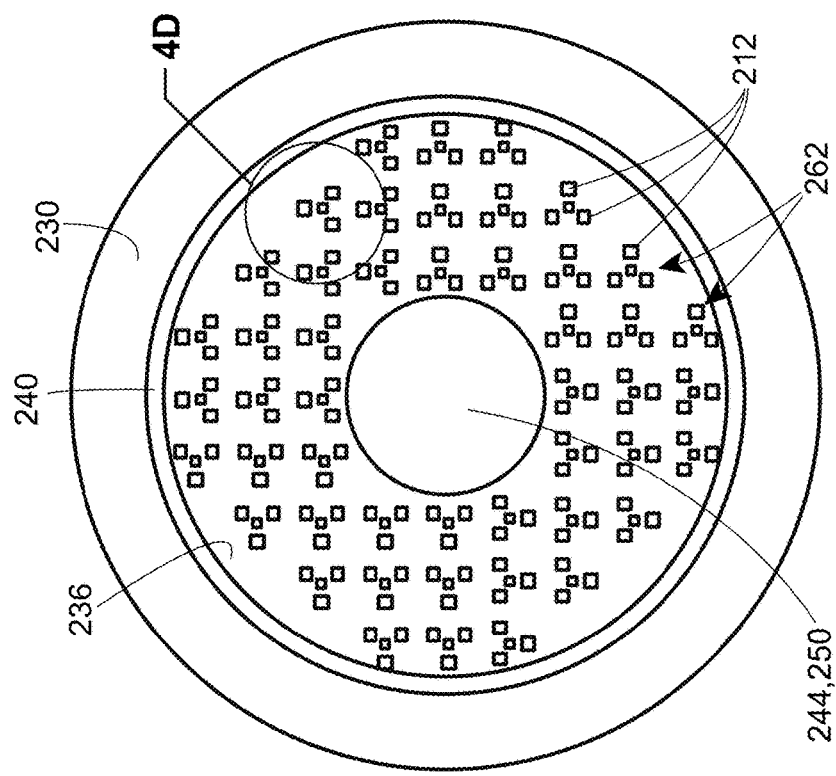
FIG. 4C is a bottom view of the lighting device of FIGS. 4A and 4B, showing a first plurality of light-emitting elements configured to deactivate pathogens.

As illustrated in FIGS. 4A-4C, the lighting device 104 can take the form of a light bulb or fixture 200. The light fixture 200 includes an enclosed housing 204, an array 208 of light-emitting elements 212 coupled to (e.g., installed or mounted on) a portion of the housing 204, a base 216 coupled to (e.g., integrally formed with) the housing 204, and an occupancy sensor 220 coupled to (e.g., disposed or arranged on) a portion of the housing 204. The occupancy sensor 220 is optimally positioned to detect motion within a pre-determined range of or distance from (e.g., 50 feet) the light 200 within the environment 100. The light fixture 200 can emit light responsive to detection data obtained by the occupancy sensor 220, as will be discussed in greater detail below.

The housing 204 is, as noted above, enclosed, thereby preventing moisture ingress into the light fixture 200 and/or contamination of the internal components of the light fixture 200. More specifically, no surface internal to the housing 204 is exposed to the environment 100, such that dangerous pathogens cannot reside on surfaces hidden from the deactivating light emitted by the light device 200. The housing 204 illustrated in FIGS. 4A-4C is made of or manufactured from aluminum or stainless steel and has a first end 224, a second end 228, an outwardly extending annular flange 230 formed at the second end 228, and an outer circumferential wall 232 extending between the first and second ends 224, 228. The outer circumferential wall 232 has a substantially conical shape, with the diameter of the circumferential wall 232 increasing in a direction from the first end 224 to the second end 228, such that the diameter of the wall 232 is larger at the second end 228 than at the first end 224.

The housing 204 also includes a circular support surface 236 and an inner circumferential wall 240 surrounding the support surface 236. The support surface 236, which at least in FIG. 4B faces downward, is arranged to receive a portion or all of the array 208 of the light-emitting elements 212. The inner circumferential wall 240, like the outer circumferential wall 232, has a substantially conical shape. The inner circumferential wall 240 is spaced radially inward of the outer circumferential wall 232 and extends between the flange 230 of the housing 204 and the support surface 236.

The housing 204 also includes a support element, which in this version takes the form of a cylindrical post 244, disposed along a center axis 248 of the light 200. The cylindrical post 244 extends outward (downward when viewed in FIG. 4B) from the support surface 236 and terminates at an end 250 positioned axially inward of the second end 228 (i.e., axially located between the first and second ends 224, 228). A cavity 252 is formed or defined proximate to the second end 228 and between the flange 230, the inner circumferential wall 240, and the cylindrical post 244.

The array 208 of light-emitting elements 212 is generally arranged on or within the enclosed housing 204. The array 208 of light-emitting elements 212 is, in this version, arranged on an outer portion of the enclosed housing 204 exposed to the environment 100. More specifically, the light-emitting elements 212 are arranged in the cavity 252, on the support surface 236 and surrounding the post 244, as illustrated in FIGS. 4B and 4C. The light-emitting elements 212 can be secured in any known manner (e.g., using fasteners, adhesives, etc.). Any number of light-emitting elements 212 can be utilized, depending on the given application (e.g., depending upon the healthcare environment 100. As an example, more light-emitting elements 212 may be utilized for larger environments 100 and/or for environments 100 particularly susceptible to high levels of dangerous pathogens.

The light-emitting elements 212 include one or more first light-emitting elements 256 and one or more second light-emitting elements 260 arranged in any number of different patterns. The light-emitting elements 212 illustrated in FIGS. 4C and 4D include a plurality of clusters 262 each having one first light-emitting element 256 surrounded by three second light-emitting elements 260. However, in other examples, the light-emitting elements 212 can be arranged differently, for example, with one or more of the clusters 262 having a different arrangement of the light-emitting elements 256 and the second light-emitting elements 260. The light-emitting elements 256 in this version take the form of light-emitting diodes (LEDs) and are configured to together (i.e., combine to) emit at least 3,000 mW of specially configured visible light, i.e., light having a wavelength in a range of between approximately 380 nm and approximately 420 nm, and more particularly, light having a wavelength between 400 nm and 420 nm. In some cases, the light-emitting elements 256 can be configured to together emit at least 5,000 mW of specially configured visible light, while in other cases, the light-emitting elements can be configured to together emit at least 10,500 mW of specially configured visible light. The light-emitting elements 260 also take the form of LEDs, at least in this version, but are configured to emit visible light that complements the visible light emitted by the light-emitted elements 256. Generally speaking, the light emitted by the light-emitting elements 260 has a wavelength greater than the wavelength of the light emitted by the light-emitting elements 256. In many cases, the light emitted by some, if not all, of the light-emitting elements 260 will have a wavelength greater than 500 nm. As an example, the light-emitting elements 260 may emit red, green, and blue light, which combine to yield or form white visible light. The total light emitted by the light-emitting elements 256 has, in many cases, a greater luminous flux than the total light emitted by the light-emitting elements 260, though this need not be the case.

In any event, the light-emitting elements 256 and 260 are configured such that the total or combined light emitted by the array 208 is white, a shade of white, or a different color that is aesthetically non-objectionable in the healthcare environment 100. Generally speaking, the total or combined light will have a color rendering index of above 70, and, more preferably, above 80 or above 90, and will have a color temperature in a range of between 1500 degrees and 7000 degrees Kelvin, preferably in a range of between 2100 degrees and 6000 degrees Kelvin, and, more preferably, in a range of between 2700 degrees and 5000 degrees Kelvin.

The base 216 is coupled proximate to, and protrudes outward from, the first end 224 of the housing 204. The base 216 in this version is a threaded base that is integrally formed with the housing 204 and is adapted to be screwed into a matching socket (not shown) provided in a receiving structure in the healthcare environment 100. The matching socket can be provided in a wall, a ceiling, a floor, a housing, or some other structure, depending upon the healthcare environment 100. In any event, as is known in the art, the threaded base 216 can include one or more electrical contacts adapted to be electrically connected to corresponding electrical contacts of the socket when the base 216 is coupled to the socket, thereby powering the light fixture 200.

It is generally desired that the base 216 be screwed into the matching socket such that at least a portion of the housing 204 is recessed into the discrete structure, thereby sealing that portion of the housing 204 from the external environment. FIGS. 5A and 5B illustrate an example of this, wherein the light fixture 200 is sealingly disposed in a receiving structure 270 provided (e.g., formed) in a ceiling, housing, or other structure in the environment 100. The receiving structure 270 has a substantially cylindrical base 272 and an outwardly extending flange 274 formed at an end 276 of the base 272. A seal (e.g., a gasket) 278 is disposed on the outwardly extending flange 274 of the receiving structure 270. When the base 216 of the light fixture 200 is screwed into a matching socket (not shown) provided in the receiving structure 270, the housing 204 of the light fixture 200 is substantially entirely disposed or recessed within the base 272 of the receiving structure 270, and the flange 230 of the light 200 sealingly engages the seal 278 disposed on the flange 274 of the receiving structure 270. In this way, the housing 204 is substantially sealed off from the outside environment 100.

With reference back to FIGS. 4A and 4B, the occupancy sensor 220, which can take the form of a passive infrared motion sensor, a microwave motion sensor, an ultrasonic motion sensor, or another type of occupancy sensor, is arranged or disposed on a downward facing portion of the housing 204. The occupancy sensor 220 in this version is disposed on the end 250 of the cylindrical post 244, which allows the occupancy sensor 220 to detect motion within a pre-determined range of or distance from (e.g., 50 feet) the light device 200 within the environment 100. In some cases, the occupancy sensor 220 can detect any motion within the environment 100 (e.g., when the environment 100 only includes one light fixture 200). As briefly discussed above, the light 200 can emit light responsive to detection data obtained by the occupancy sensor 220. More specifically, the light fixture 200 can adjust the outputted light in response to detection data obtained by the occupancy sensor 220. When, for example, the occupancy sensor 220 does not detect any motion within the pre-determined range or distance, the light device 200 device can shut off or emit less light from the second light-emitting elements 260, as the healthcare environment 100 is not occupied (and, therefore, the color of the emitted light may not matter). In other words, the light 200 can emit light only from the first light-emitting elements 256, thereby deactivating dangerous pathogens while using less power. Conversely, when the occupancy sensor 220 detects motion within the pre-determined range or distance, the light fixture 200 can emit light from both the first and second light-emitting elements 256, 260, thereby ensuring that the aesthetically unobjectionable light (e.g., white light) is provided to the occupied healthcare environment 100 and, at the same time, the light fixture 200 continues to deactivate dangerous pathogens, even while the environment 100 is occupied.

With reference still to FIGS. 4A and 4B, the light fixture or bulb 200 also includes an annular refractor 280. The refractor 280 in this version is a nano-replicated refractor film mounted to the inner circumferential wall 240 of the housing 204. The refractor 280 can be secured there via any known manner (e.g., using a plurality of fasteners, using adhesives, etc.). So disposed, the refractors 280 surrounds or circumscribes the first and second light-emitting elements 256, 260, such that the refractor 280 helps to focus and evenly distribute light emitted from the light 200 to the environment 100. If desired, the refractor 280 can be arranged differently or other types of refractors can instead be utilized so as to yield different controlled light distributions.

Although not depicted herein, it will be understood that one or more drivers (e.g., LED drivers), one or more other sensors (e.g., a daylight sensor), one or more lenses, one or more reflectors, one or more boards (e.g., a printed circuit board, a user interface board), wiring, various control components (e.g., a local controller communicatively connected to the server 66), one or more communication modules (e.g., one or more antennae, one or more receivers, one or more transmitters), and/or other electrical components can be arranged or disposed within or proximate to the enclosed housing 204. The communication modules can include one or more wireless communication modules and/or one or more wired communication modules. The one or more communication modules can thus facilitate wireless and/or wired communication, using any known communication protocol(s), between components of the light bulb or fixture 200 and the local controller, the server 66, and/or other control system components. More specifically, the one or more communication modules can facilitate the transfer of various data, such as occupancy or motion data, operational instructions (e.g., turn on, turn off, dim, etc.), etc., between the components of the bulb or fixture 200 and the local controller, the server 66, other lighting devices 58, and/or other control system components. For example, data indicative of when light is emitted from the light-emitting elements 256, 260 can be monitored and transmitted to the server 66 via such communication modules. As another example, data indicative of how much light is emitted from the light-emitting elements 256, 260 over a pre-determined period of time (e.g., during a specific surgical procedure) can be monitored and transmitted to the server 66 via such communication modules.

In other versions, the light bulb or fixture 200 can be constructed differently. Specifically, the housing 204 can have a different size, shape, and/or be made of one or more materials other than or in addition to aluminum or stainless steel. For example, the housing 204 can have a rectangular, square, triangular, irregular, or other suitable shape. In one version, the housing 204 may not include the post 244 and/or the post 244 may take on a different shape and/or size than the cylindrical post 244 illustrated in FIGS. 4A and 4B.

Figure 6B:
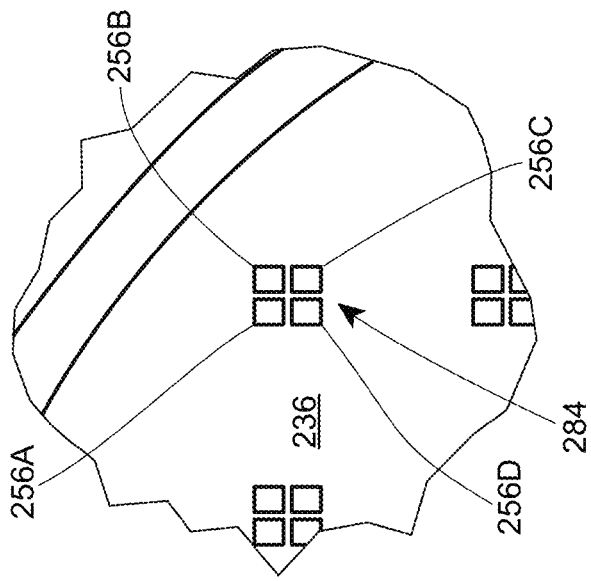
FIG. 6B is a partial, close-up view of a portion of the lighting device of FIG. 6A.
Figure 6A:
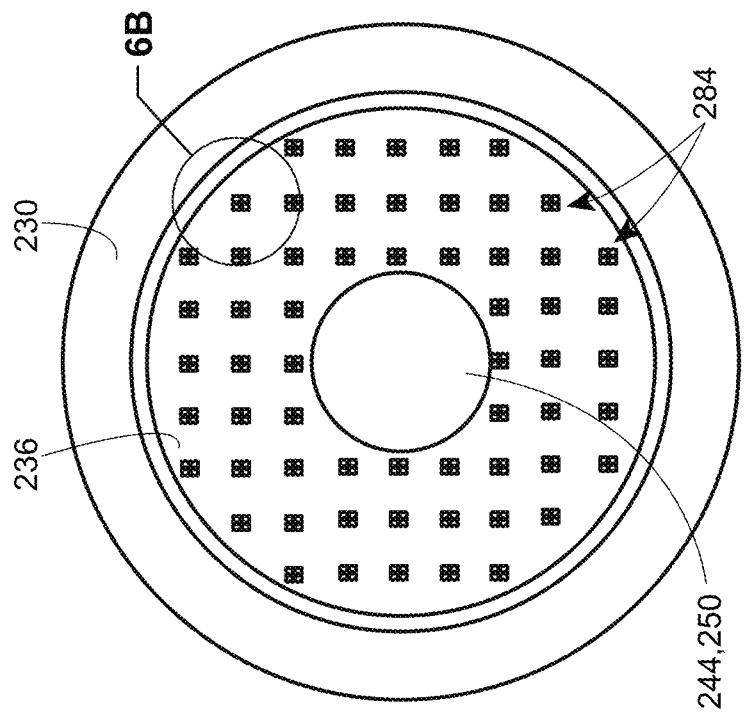
FIG. 6A is a bottom view of another exemplary version of the lighting device of FIG. 2, showing a second plurality of light-emitting elements configured to deactivate pathogens.

Moreover, the array 208 of light-emitting elements 212 can vary. In some versions, the array 208 (or portions thereof) can be arranged within or on a different portion of the housing 204. In some versions, the array 208 of light-emitting elements 212 may only include the first light-emitting elements 256, which, as noted above, are configured to emit specially configured spectrum visible light at a sufficiently high power level. In these versions, one or more of the light-emitting elements 256 can be covered or coated with phosphors, substrates infused with phosphors, and/or one or more other materials and/or media so as to yield light having a higher wavelength than the specially configured narrow spectrum visible light, such that the total or combined light emitted by the array 208 is white, a shade of white, or a different color that is aesthetically non-objectionable in the healthcare environment 100. FIGS. 6A and 6B depict one such version, wherein the light-emitting elements 212 include a plurality of clusters 284 of four light-emitting elements 256, with three of the light-emitting elements 256A, 256B, and 256C being covered or coated with phosphors, and one of the light-emitting elements 256D being uncovered (i.e., not coated with a phosphor). In the illustrated version, the three light-emitting elements 256A, 256B, and 256C are covered or coated with blue, red, and green phosphors, respectively, such that the total or combined light emitted by each cluster 284 (and, thus, the array 208) is white, a shade of white, or a different color that is aesthetically non-objectionable in the healthcare environment 100. It will be appreciated that in other versions, more or less of the light-emitting elements 256 can be covered with phosphors, the light-emitting elements 256 can be covered with different colored phosphors, and/or the light-emitting elements 256 can be arranged differently relative to one another (i.e., the clusters 284 can vary). In yet other versions, the array 208 can include additional light-emitting elements, e.g., LEDs configured to emit specially configured visible light at a sufficiently high power level, configured to be turned on only when no motion is detected in the environment 100 (for even greater room dosage). Finally, it will be appreciated that the first and/or second light-emitting elements 256, 260 can, instead of being LEDs, take the form of fluorescent, incandescent, plasma, or other light-elements.

Figure 7:
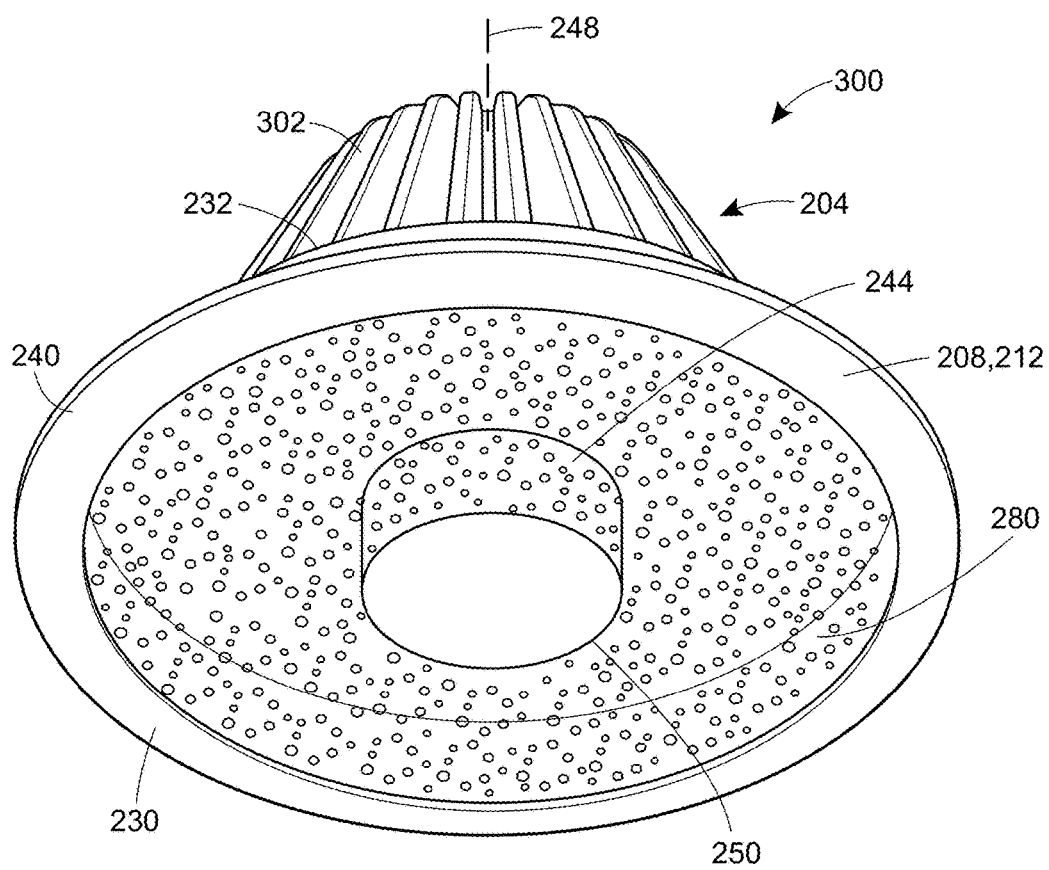
FIG. 7 illustrates another exemplary version of the lighting device of FIG. 2.

FIG. 7 illustrates another version of the lighting device 104. As illustrated in FIG. 7, the lighting device 104 can take the form of a light bulb or fixture 300. The light fixture 300 is substantially similar to the light fixture 200, with common reference numerals used to refer to common components. However, unlike the light 200, the light 300 includes a heat sink 302 formed on an exterior surface of the light 300 and configured to dissipate heat generated by the light fixture 300, and, more particularly, the light-emitting elements 212. In some cases, the heat sink 302 can be coupled (e.g., mounted, attached) to and around a portion of the outer circumferential wall 232, while in other cases the heat sink 302 can be integrally formed with the housing 204 (in which case the heat sink 302 may take the place of some or all of the wall 232).

Figure 8:
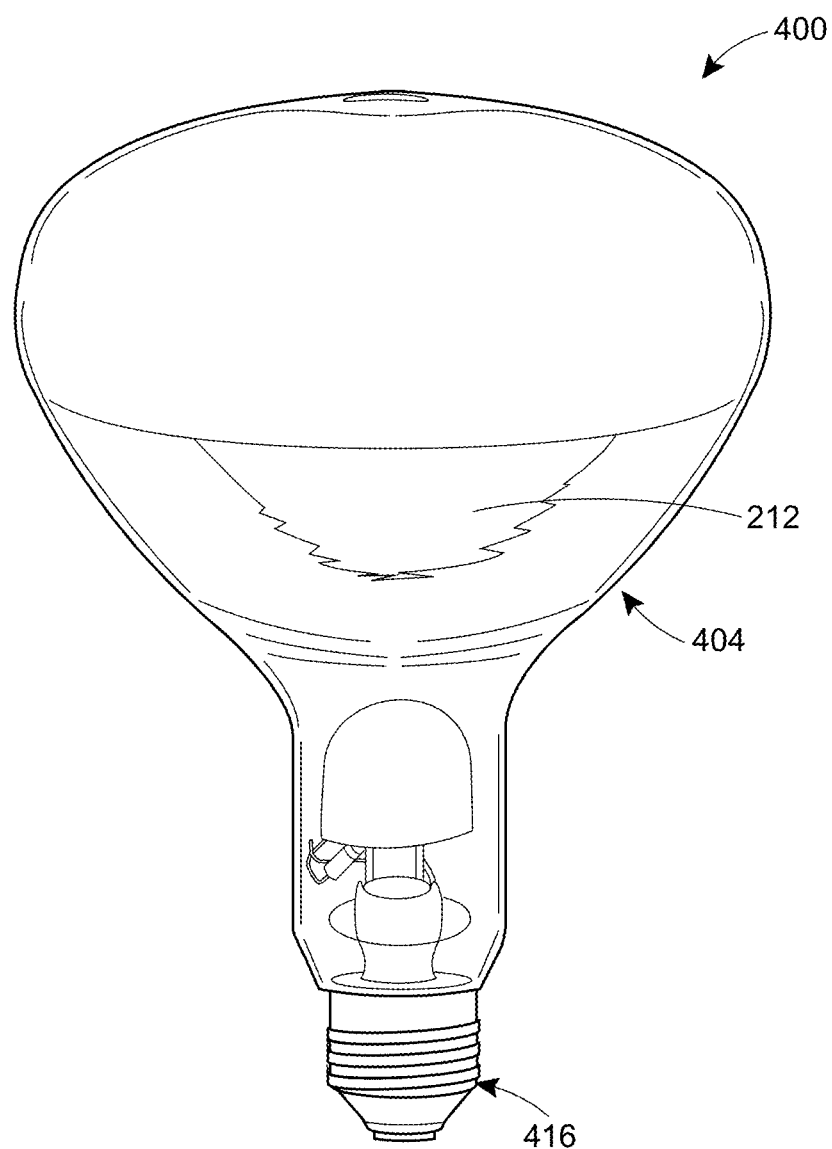
FIG. 8 illustrates another exemplary version of the lighting device of FIG. 2.

FIG. 8 illustrates yet another version of the lighting device 104. As illustrated in FIG. 7, the lighting device 104 can take the form of a light bulb or fixture 400. The light 400 includes an enclosed housing 404 that is different from the housing 204 of the lights 200, 300. The enclosed housing 404 is, in this version, is made of or manufactured from glass or plastic and is shaped like a housing of a conventional incandescent light bulb. The light 400 also includes a base 416, which is similar to the base 216 described above. However, unlike a conventional incandescent light bulb, the light 400 also includes the light-emitting elements 212, which are arranged within the enclosed housing 404 and, as discussed above, are configured to provide specially configured narrow spectrum visible light at power levels sufficiently high enough to effectively deactivate dangerous pathogens, all while providing an output of quality light that is unobjectionable.

FIGS. 9A-9D illustrate yet another version of the lighting device 104, in the form of a light fixture 500. The light fixture 500 includes a housing or chassis 504, a plurality of light-emitting elements 512 coupled to (e.g., installed or mounted on) a portion of the housing 504, a lens 514 configured to diffuse light emitted by the light-emitting elements 512 in an efficient manner, a pair of support arms 516 coupled to (e.g., integrally formed with) the housing 504, and a control device in the form of a local controller 520 that is identical to the controller 120 described above. It will be appreciated that the light fixture 500 also includes an occupancy sensor, a daylight sensor, a communication module, and a dosing feedback system; these components are, however, identical to the motion sensor 108, the daylight sensor 112, the communication module 116, and the dosing feedback system 124, respectively, described above, so are, for the sake of brevity, not illustrated in FIGS. 9A-9C and are not described in any further detail below. The light fixture 500 may also include any of the means for maintaining junction temperature discussed above in connection with the lighting device 104.

Figure 9A:
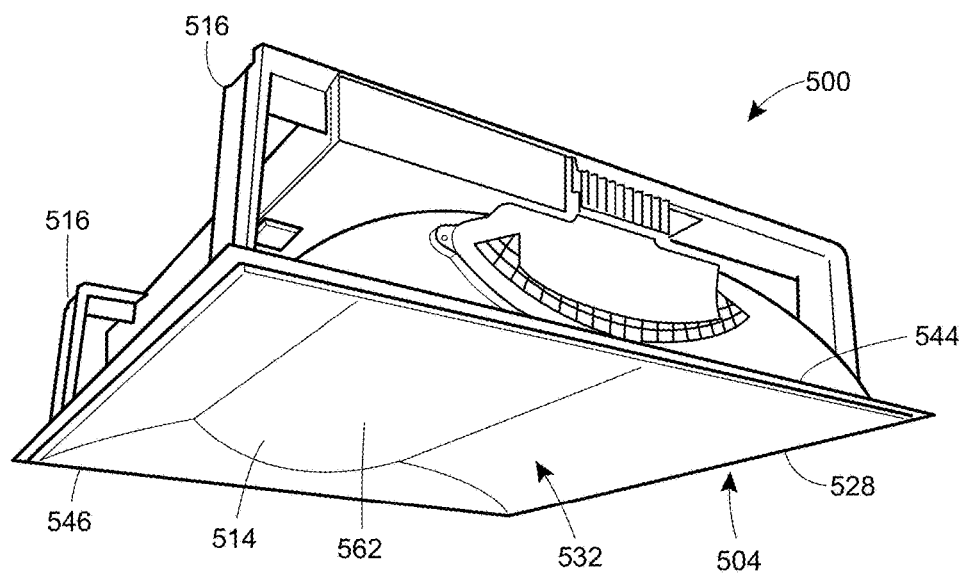
FIG. 9A is a perspective view of another exemplary version of the lighting device of FIG. 2.
Figure 9B:
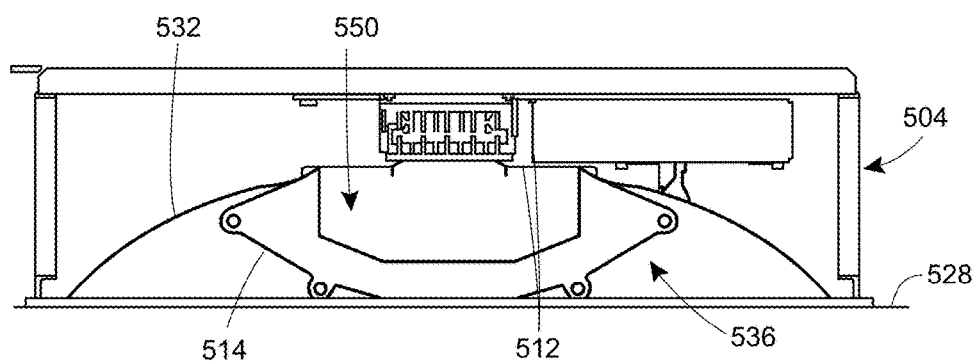
FIG. 9B is a cross-sectional view of the lighting device of FIG. 9A.
Figure 9C:
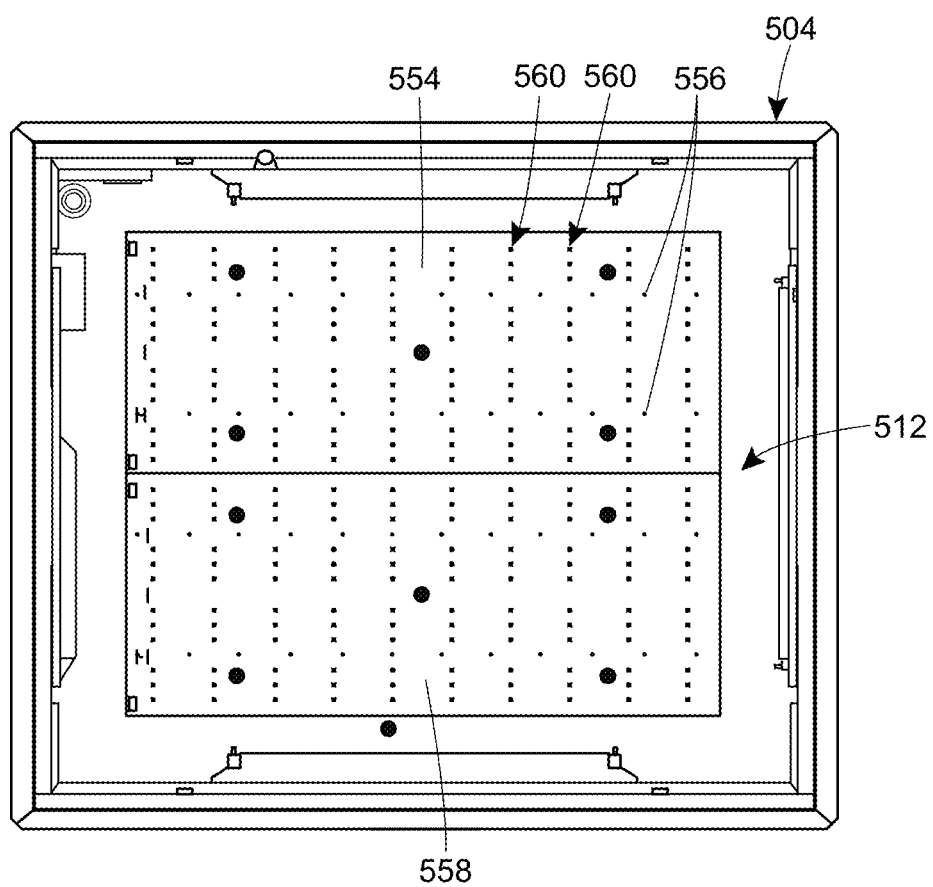
FIG. 9C is another cross-sectional view of the lighting device of FIG. 9A, showing a first plurality of light-emitting elements configured to emit light that deactivates pathogens and a second plurality of light-emitting elements configured to emit light that blends with light emitted by the first plurality of light-emitting elements to produce a visually appealing visible light.

The housing 504 in this version is made of or manufactured from steel (e.g., 18-gauge welded cold-rolled steel) and has a substantially rectangular flange 528 that surrounds a curved, interior support surface 532, which at least in FIG. 9B faces downward. The rectangular flange 528 and the curved, interior support surface 532 together define a cavity 536 sized to receive the lens 514, which in this example is a Frost DR Acrylic lens manufactured by Kenall Manufacturing. The support arms 516 are coupled to an exterior portion of the housing 504 proximate to the flange 528, with one support arm 516 coupled at or proximate to a first end 544 of the housing 504 and the other support arm 516 coupled at or proximate to a second end 546 of the housing 504 opposite the first end 536. The support arms 516 are thus arranged to facilitate installation of the light fixture 500, e.g., within a ceiling of the environment 100.

The light-emitting elements 512 are generally arranged on or within the housing 504. The light-emitting elements 512 are, in this version, arranged in a sealed or closed light-mixing chamber 550 defined by the housing 504 and the lens 540. The light-emitting elements 512 can be secured therein any known manner (e.g., using fasteners, adhesives, etc.). The light-emitting elements 512 in this version include a plurality of first light-emitting elements in the form of a plurality of first LEDs 556 and a plurality of second light-emitting elements in the form of a plurality of second LEDs 560. The light-emitting elements 512 can be arranged on first and second LED modules 554, 558 in the manner illustrated in FIG. 9C, with the second LEDs 560 clustered together in various rows and columns, and the first LEDs 556 arranged between these rows and columns, or can be arranged in a different manner. In one example, ninety-six (96) first LEDs 556 and five-hundred seventy-six (576) second LEDs 560 are used, for a ratio of first LEDs 556 to second LEDs 560 equal to 1:6. In other examples, more or less first and second LEDs 556, 560 can be employed, with different ratios of first LEDs 556 to second LEDs 560. As an example, the ratio of first LEDs 556 to second LEDs 560 may be equal to 1:3, 1:2, 1:1, or some other ratio, depending upon the power capabilities of the first and second LEDs 556, 560.

The first LEDs 556 are, like the light-emitting elements 256, configured to provide (e.g., emit) specially configured visible light, i.e., light having a wavelength in a range of between approximately 380 nm and approximately 420 nm, and more particularly in a range of between 400 nm and 420 nm, with the combination or sum of the first LEDs 556 configured to provide or deliver (e.g., emit) sufficiently high levels of the specially configured visible light so as to deactivate pathogens surrounding the light fixture 500. As discussed above, the first LEDs 556 may together (i.e., when summed) emit at least 3,000 mW of the specially configured visible light, e.g., 3,000 mW, 4,000 mW, 5,000 mW, or some other level of visible light above 3,000 mW. The minimum integrated irradiance of the specially configured visible light emitted or otherwise provided by all of the LEDs 556, which, at least in this example, is measured from any exposed surface or unshielded point in the environment 100 that is 1.5 m from any point on any external-most luminous surface 562 of the lighting device 504, may be equal to 0.01 mW/cm$^2$, 0.02 mW/cm$^2$, 0.05 mW/cm$^2$, 0.1 mW/cm$^2$, 0.15 mW/cm$^2$, 0.20 mW/cm$^2$, 0.25 mW/cm$^2$, 0.30 mW/cm$^2$, or some other value greater than 0.01 mW/cm$^2$. In other examples, the minimum integrated irradiance of the specially configured visible light may be measured from a different distance from any external-most luminous surface 562, nadir, or any other unshielded or exposed surface in the environment 100. The second LEDs 560 are, like the light-emitting elements 260, configured to emit visible light, but the second LEDs 560 emit light having a wavelength that is greater than the wavelength of the light emitted by the one or more first LEDs 556. The light emitted by the second LEDs 560 will generally have a wavelength that is greater than 500 nm, though this need not be the case.

In any event, the light emitted by the second LEDs 560 complements the visible light emitted by the one or more first LEDs 556, such that the combined or blended light output formed in the mixing chamber 550 is a white light having the properties discussed above (e.g., white light having a CRI of above 80, a color temperature in a range of between 2100 degrees and 6000 degrees, and/or (u',v') coordinates on the 1976 CIE Chromaticity Diagram that lie on a curve that is between 0.035 Duv below and 0.035 above a planckian locus defined by the ANSI C78.377-2015 color standard). As a result, the combined or blended light output by the light fixture 500 is aesthetically pleasing to humans, as illustrated in, for example, FIG. 9E.

With reference back to FIG. 9D, the lighting device 504 also includes a first LED driver 564 and a second LED driver 568 each electrically connected to the controller 520 and powered by external power (e.g., AC power) received from an external power source (not shown). Responsive to instructions or commands received from the controller 520, the first LED driver 564 is configured to power the first LEDs 556, while the second LED driver 568 is configured to power the second LEDs 560. In other examples, the lighting device 564 can include more or less LED drivers. As an example, the lighting device 564 can include only one LED driver, configured to power the first LEDs 556 and the second LEDs 560, or can include multiple LED drivers configured to power the first LEDs 556 and multiple LED drivers configured to power the second LEDs 560.

Figure 9D:
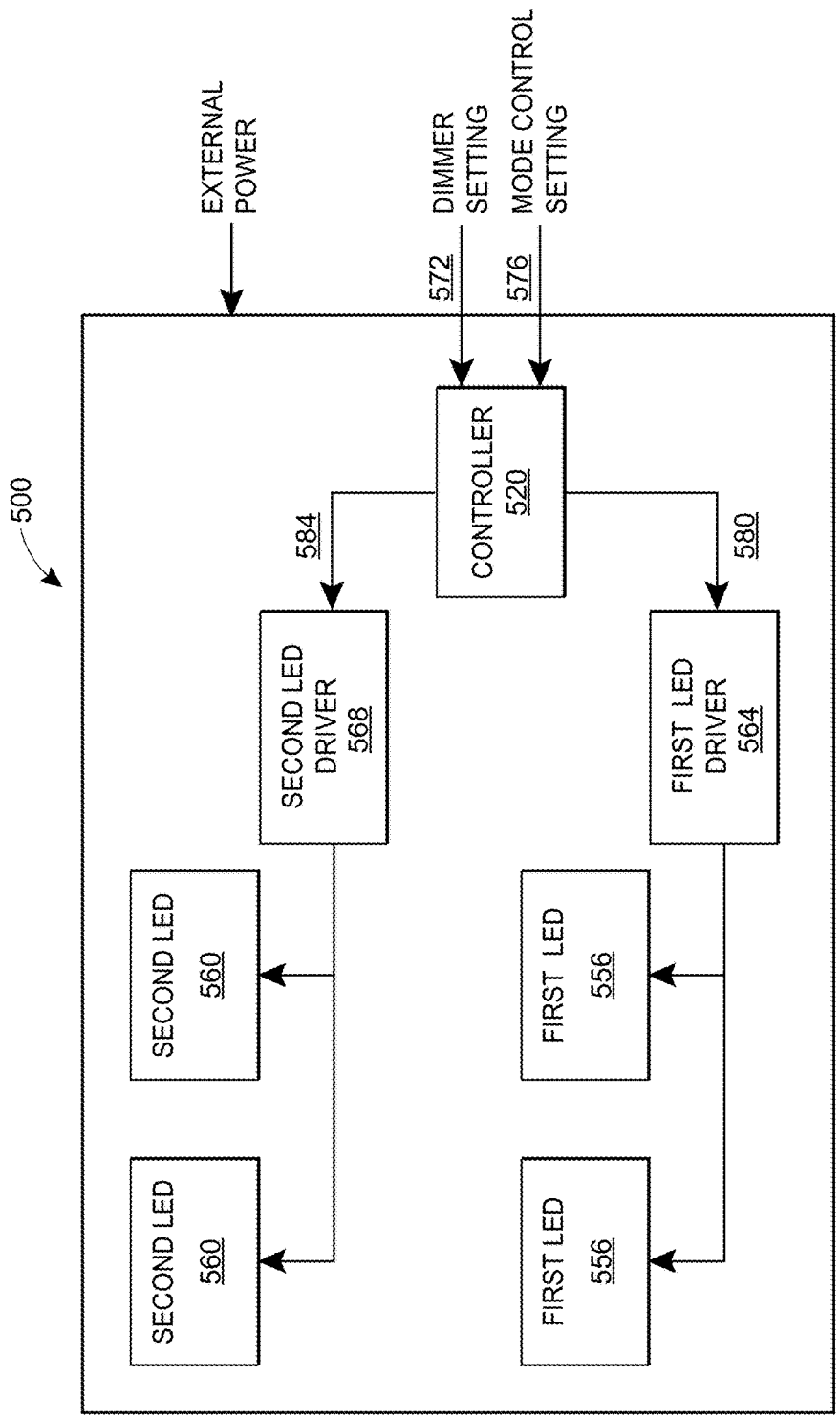
FIG. 9D is a block diagram of various electrical components of the lighting device of FIG. 9A.

As also illustrated in FIG. 9D, the controller 520 may receive a dimmer setting 572 and/or a mode control setting 576 received from a user of the lighting device 504 (e.g., input via a dimming switch electrically connected to the light fixture 500) and/or a central controller via, e.g., the server 66. The dimmer setting 572 is a 0-10 V control signal that specifies the desired dimmer or dimming level for the lighting device, which is a ratio of a desired combined light output of the first and second LEDs 556, 560 to the maximum combined light output of the first and second LEDs 556, 560 (and which corresponds to the blended or combined output discussed above). The 0 V input generally corresponds to a desired dimming level of 100% (i.e., no power is supplied to the first LEDs 556 or the second LEDs 560), the 5 V input generally corresponds to a desired dimming level of 50%, and the 10 V input generally corresponds to a desired dimming level of 0% (i.e., the first and second LEDs 556, 560 are fully powered), though this need not be the case. The mode control setting 576 is a control signal that specifies the desired operating mode for the lighting device 504. The mode control setting 576 may, for example, specify that the lighting device 504 be in a first mode (e.g., an examination mode, a disinfection mode, a blended mode), whereby the first and second LEDs 556, 560 are fully powered, or a second mode (e.g., a nighttime mode), whereby the second LEDs 560 are powered while the first LEDs 556 are not powered (or are powered at a lower level). Other modes and/or modes corresponding to different power settings or levels may be utilized.

In operation, the light fixture 500 provides or outputs (e.g., emits) light based on or in response to commands or instructions from the local controller 520. More specifically, the first LED driver 564 and/or the second LED driver 568 power the first LEDs 556 and/or the second LEDs 560, such that the first LEDs 556 and/or the second LEDs 560 provide or output (e.g., emit) a desired level of light, based on or in response to commands or instructions to that effect received from the local controller 520. These commands or instructions may be generated based on or responsive to receipt of the dimmer setting 572, receipt of the mode control setting 576, occupancy data obtained by the occupancy sensor and/or daylight data obtained by the daylight sensor, and/or based on or responsive to commands or instructions received from the server 66 and/or the client devices 70. Thus, the light fixture 500, and more particularly the first LEDs 556 and/or the second LEDs 560, may provide (e.g., emit) light responsive to occupancy data obtained by the occupancy sensor, daylight data obtained by the daylight sensor, and/or other commands or instructions (e.g., timing settings, dimmer settings, mode control settings).

The light fixture 500 can, for example, responsive to data indicating that the environment 100 is occupied, data indicating that there is a more than pre-determined amount of natural light in the environment 100 (i.e., it is daytime), and/or various commands and instructions, emit light from the first LEDs 556 and the second LEDs 560, thereby producing a blended or combined output of white visible light discussed above. In turn, the light fixture 500 produces a visible white light that effectively deactivates dangerous pathogens in the environment 100, and, at the same time, illuminates the environment 100 in a safe and objectionable manner (e.g., because the environment 100 is occupied, it is daytime, and/or for other reasons).

Figure 9F:
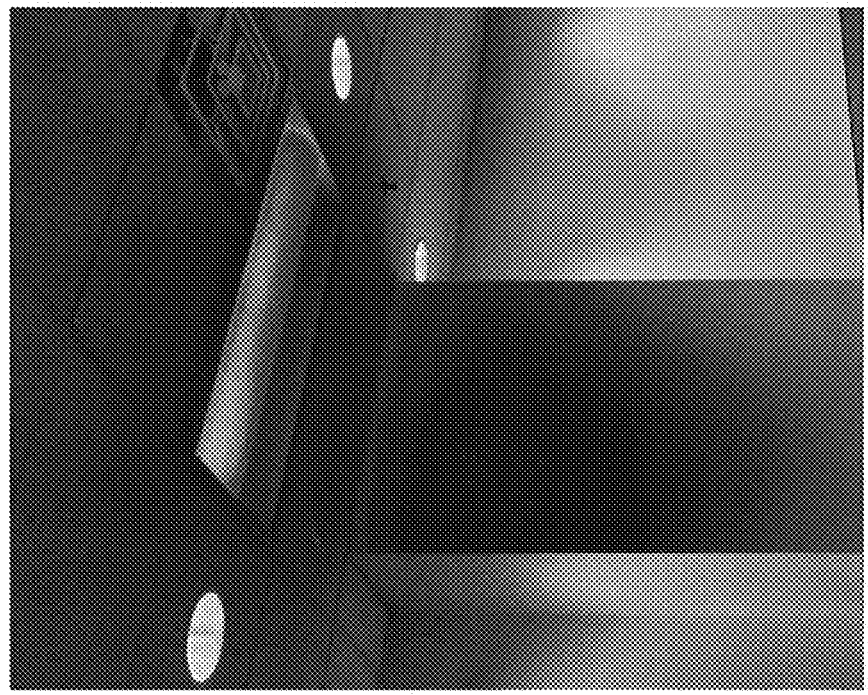
FIG. 9F illustrates disinfecting light that can be output by the lighting device of FIG. 9A when the environment is not occupied.
Figure 9E:
FIG. 9E illustrates visually appealing white visible light that can be output by the lighting device of FIG. 9A when the environment is occupied.

However, responsive to data indicating that the environment 100 is not occupied or has been unoccupied for a pre-determined amount of time (e.g., 30 minutes, 60 minutes), the light fixture 500 can reduce the power of the second LEDs 560, such that a substantial portion of the output light is from the first LEDs 556, or shut off the second LEDs 560 (which are no longer needed to produce a visually appealing blended output since the environment 100 is unoccupied), such that light is only emitted from the first LEDs 556, as illustrated in FIG. 9F. The light fixture 500 can, at the same time, increase the power or intensity of the first LEDs 556 and, in some cases, can activate one or more third LEDs that are not shown but are configured, like the LEDs 556, to emit sufficiently high levels of specially configured visible light, i.e., light having a wavelength in a range of between approximately 380 nm and approximately 420 nm, and more particularly between 400 nm and 420 nm. In this manner, the deactivation effectiveness of the light fixture 500 can be increased (without sacrificing the visual appeal of the light fixture 500, as the environment 100 is unoccupied) and, at the same time, the energy consumption of the light fixture 500 can be reduced, or at the very least maintained (by virtue of the first LEDs 556 being reduced or shut off).

In some cases, the light fixture 500 can, responsive to data indicating that the environment 100 is not occupied or has been unoccupied for a period of time less than a pre-determined amount of time (e.g., 30 minutes), provide or output the combined or blended light output (of the first and second LEDs 556, 560) discussed above. This provides a fail-safe mode that ensures that the environment 100 is indeed vacant before the second LEDs 560 are shut off or reduced.

The light fixture 500 can respond in a similar or different manner to data indicating that there is more than a pre-determined amount of natural light in the environment 100, such that there is no need for the light from the second LEDs 560, or there is less than a pre-determined amount of natural light in the environment 100 (i.e., it is nighttime, such that the environment 100 is unlikely to be occupied). If desired, the light fixture 500 may only respond in this manner responsive to data indicating that the environment 100 is unoccupied and data indicating that it is nighttime. Alternatively, the light fixture 500 may only respond in this manner responsive to timer settings (e.g., it is after 6:30 P.M.) and/or other commands or instructions.

The light fixture 500, and more particularly the first LEDs 556 and the second LEDs 560, can also be controlled responsive to settings such as the dimmer setting 572 and the mode control setting 576 received by the controller 520. Responsive to receiving the dimmer setting 572 or the mode control setting 576, the controller 520 causes the first and second LED drivers 564, 568 to power (or not power) the first and second LEDs 556, 560, respectively, in accordance with the received setting. More specifically, when the controller 520 receives the dimmer setting 572 or the mode control setting 576, the controller 520 instructs the first LED driver 564, via a first LED control signal 580, and instructs the second LED driver 568, via a second LED control signal 584, to power (or not power) the first and second LEDs 556, 560 according to the desired dimming level specified by the dimmer setting 572 or the desired operating mode specified by the mode control setting 576.

Figure 9G:
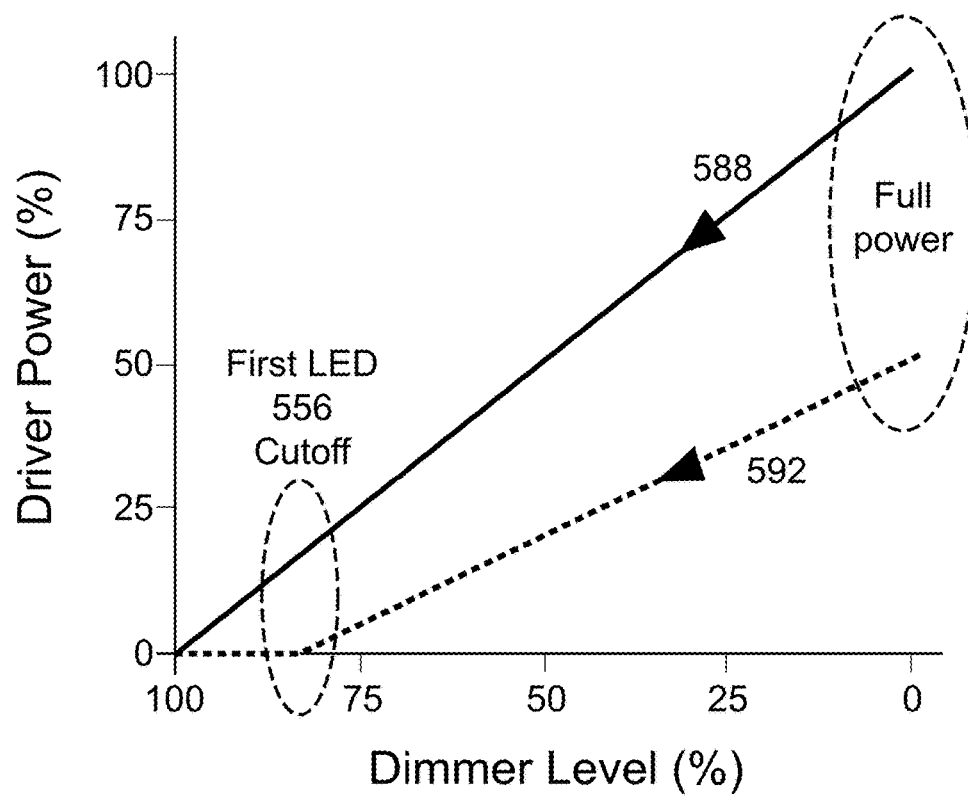
FIG. 9G illustrates one example of how the lighting device of FIGS. 9A-9D can be controlled responsive to various dimming settings.

FIG. 9G illustrates one example of how the controller 520 can control the first and second LED drivers 564, 568 responsive to various dimmer settings 572 that specify various dimming levels (e.g., 0%, 25%, 50%, 75%, 100%). Generally speaking, the controller 520 causes the first and second LED drivers 564, 568 to increase the total light output by the first and second LEDs 556, 560 responsive to decreasing dimming levels, thereby increasing the color temperature of the total light output, and causes the first and second LED drivers 564, 568 to decrease the total light output by the first and second LEDs 556, 560 responsive to increasing dimming levels, thereby decreasing the color temperature of the total light output. But, as shown in FIG. 9G, the controller 520 controls the first LEDs 556 (via the first LED driver 564) differently than it controls the second LEDs 560 (via the second LED driver 568). In other words, there exists a non-linear relationship between the amount of light emitted by the first LEDs 556 and the amount of light emitted by the second LEDs 560 at various dimming levels. This relationship is illustrated by the fact that a first curve 588, which represents the total power supplied to the first and second LEDs 556, 560 by the first and second LED drivers 564, 568, respectively, as a function of various dimmer levels, is not parallel to or with a second curve 592, which represents the power supplied to the first LEDs 556 as a function of the same varying dimmer levels. As an example, (i) when the dimmer setting 572 specifies a dimmer level of 0% (i.e., no dimming), such that the light fixture 500 is operated at full (100%) power, approximately 50% of that total power is supplied to the first LEDs 556, (ii) when the dimmer setting 572 specifies a dimmer level of 50%, such that the light fixture 500 is operated at half (50%) power, less than 50% of that total power is supplied to the first LEDs 556, and (iii) when the dimmer setting 572 specifies a dimmer level of greater than 75% but less than 100%, such that the light fixture 500 is operated at a power less than 25%, no power is supplied to the first LEDs 556.

As a result, the first LEDs 556 are turned completely off before the second LEDs 560 are turned completely off. In this manner, the light output by the light fixture 500 remains unobjectionable and aesthetically pleasing, even while the light fixture 500 is dimmed, particularly when dimmed to very high levels (e.g., 80%, 85%, 90%, 95%).

Figure 10B:
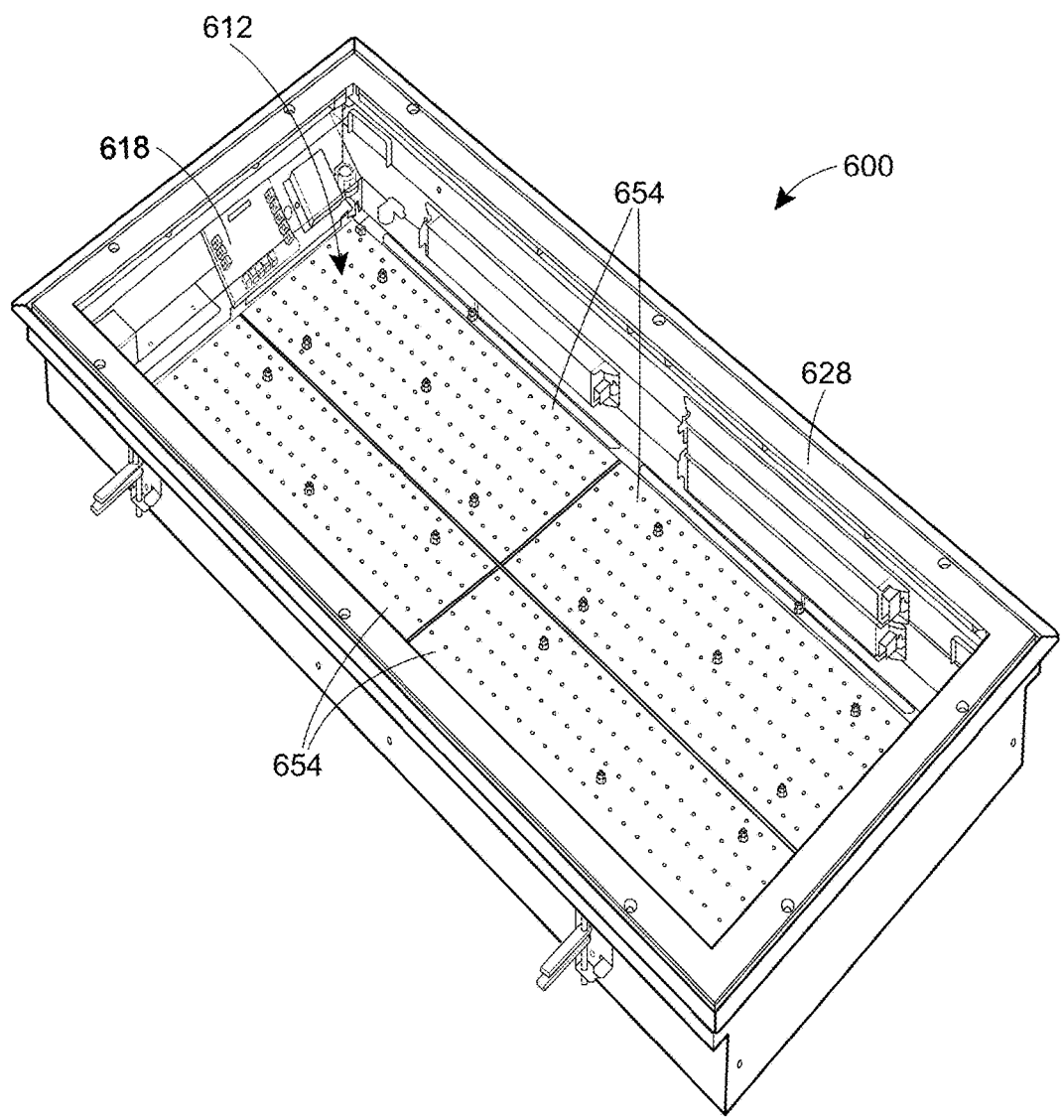
FIG. 10B is similar to FIG. 10A, but with a lens of the lighting device removed so as to show a plurality of lighting elements.
Figure 10C:
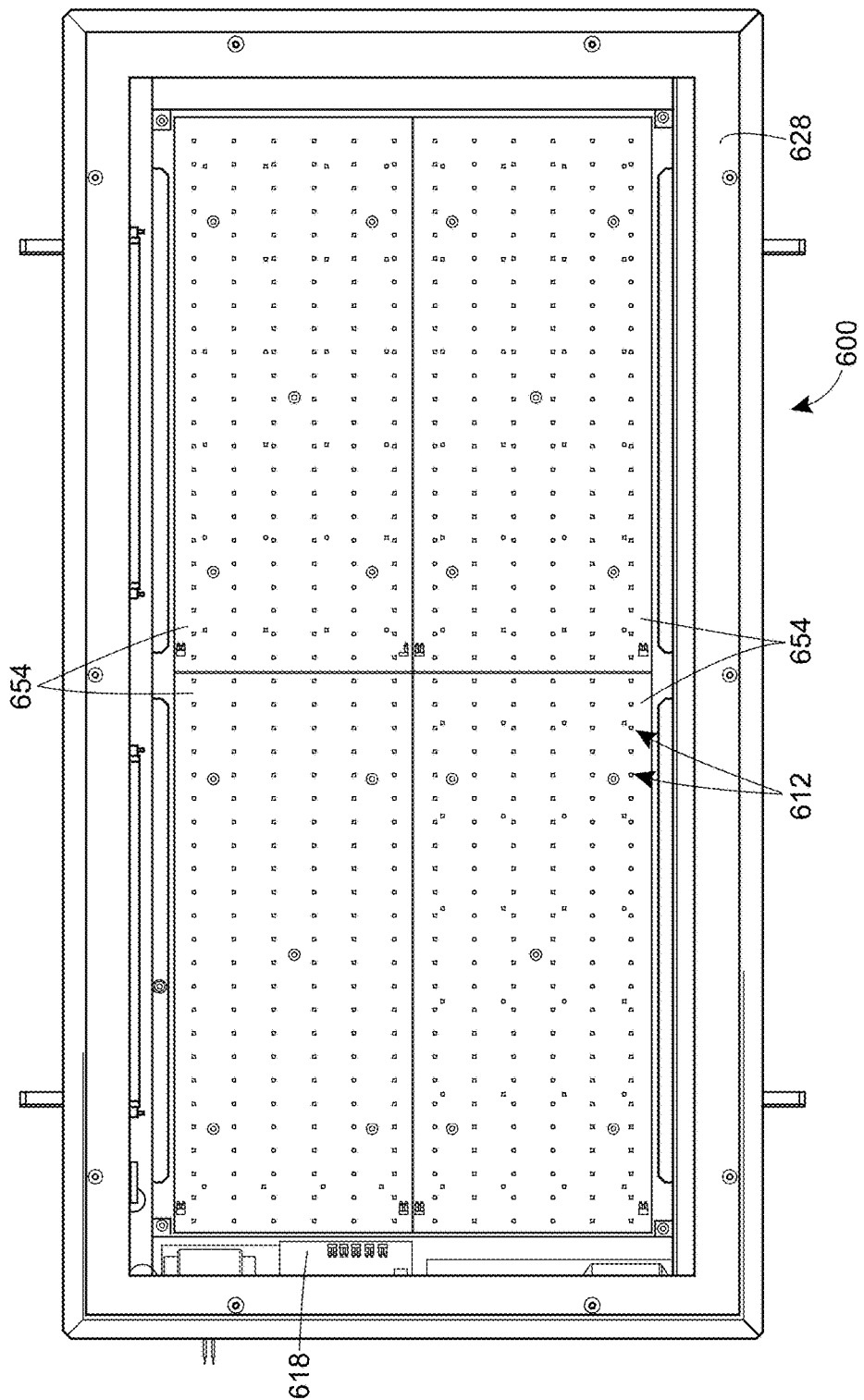
FIG. 10C is a top view of FIG. 10B.
Figure 10D:
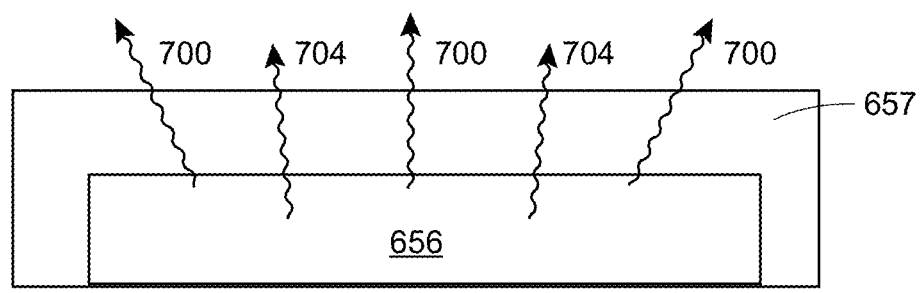
FIG. 10D is a close-up view of one of the plurality of lighting elements of FIGS. 10B and 10C.

FIGS. 10A-10D illustrate yet another version of the lighting device 104, in the form of a light fixture 600. The light fixture 600 is similar to the light fixture 500 in that it includes a housing or chassis 604 (with a flange 628) and a lens 614 configured to diffuse light emitted by the light fixture in an efficient manner, as well as components like a local controller 618, an occupancy sensor, a communication module, and a dosing feedback system identical to the controller 120, the sensor 108, the module 116, and the dosing feedback system 124, respectively described above; thus, for the sake of brevity, these components will not be described in any further detail. The light fixture 600 may also include any of the means for maintaining junction temperature discussed above in connection with the lighting device 104. However, the light fixture 600 includes a plurality of lighting elements 612 that is different from the plurality of light emitting elements 512 of the light fixture 500. While the lighting elements 612 are, like the elements 512, arranged on LED modules 654 in a sealed or closed light-mixing chamber defined by the housing 604 and the lens 614, as illustrated in FIGS. 10B and 10C, each of the lighting elements 612 takes the form of a light-emitting diode ("LED") 656 and a light-converting element 657 that is associated therewith and is configured to convert a portion of the light emitted by the LED 656, as illustrated in FIG. 10D. In this version, each LED module 654 includes seventy-six (76) lighting elements 612, though in other versions, more or less lighting elements 612 can be employed (and/or additional LEDs 656 can be employed without light-converting elements 657). In this version, the light-converting element 657, which may for example be a phosphor element such as a phosphor or a substrate infused with phosphor, covers or coats the LED 656, though in other versions the light-converting element 657 may be located remotely from the LED 656 (e.g., a remote phosphor element).

In operation, the LEDs 656 of the lighting elements 612 emit disinfecting light (e.g., light having a wavelength of between 400 nm and 420 nm) that, when combined or summed, produces power levels sufficient to deactivate pathogens. As discussed above, the LEDs 656 may combine to emit at least 3,000 mW of the disinfecting light, e.g., 3,000 mW, 4,000 mW, 5,000 mW, or some other level of visible light above 3,000 mW. At least a first portion or component 700 (and in FIG. 10D, multiple components 700) of the disinfecting light emitted by each LED 656 travels or passes through the respective light-converting element 657 without alteration, while at least a second portion or component 704 (and in FIG. 10D, multiple components 704) of the disinfecting light emitted by each LED 656 is (are) converted by the respective light-converting element 657 into light having a wavelength of greater than 420 nm. In many cases, the second portion(s) or component(s) 704 of light is (are) converted into yellow light, i.e., light having a wavelength of between 570 nm and 590 nm. In other words, each lighting element 612 is configured to provide light, at least a first component of the light, provided by the respective LED 656, having a wavelength of between 400 nm and 420 nm and at least a second component of the light, provided by the respective light-converting element 657, having a wavelength of greater than 420 nm. The first component(s) of the provided light will, as is also described above, have a minimum integrated irradiance, measured, at least in this example, from any exposed surface or unshielded point in the environment 100 that is 1.5 m from any point on any external-most luminous surface 662 of the lighting device 504, equal to 0.01 mW/cm$^2$, 0.02 mW/cm$^2$, 0.05 mW/cm$^2$, 0.1 mW/cm$^2$, 0.15 mW/cm$^2$, 0.20 mW/cm$^2$, 0.25 mW/cm$^2$, 0.30 mW/cm$^2$, or some other value greater than 0.01 mW/cm$^2$. In other examples, the minimum integrated irradiance can be measured from a different distance from any point on any external-most luminous surface 662, nadir, or some other exposed surface or point in the environment 100.

At the same time, the light provided or output by the light fixture 600, and more particularly each lighting element 612, is a white light having the properties discussed above, such that the provided light is aesthetically pleasing, or at least unobjectionable, to humans. This is because the light provided by the light converting elements 657, i.e., the second component(s), complements the disinfecting light that is emitted by the LEDs 656 and passes through the light converting elements 657 without alteration, i.e., the first component(s).

As with the light fixture 500, the light fixture 600 can provide or output light based on or in response to commands or instructions from the local controller 618. These commands or instructions may be generated based on or responsive to occupancy data obtained by the occupancy sensor and/or daylight data obtained by the daylight sensor, and/or based on or responsive to commands or instructions received from a user of the light fixture 600 (e.g., via the client devices 70) and/or the server 66. Thus, the light fixture 600 may provide light responsive to occupancy data obtained by the occupancy sensor, daylight data obtained by the daylight sensor, and/or other commands or instructions (e.g., timing settings).

Figure 11A:
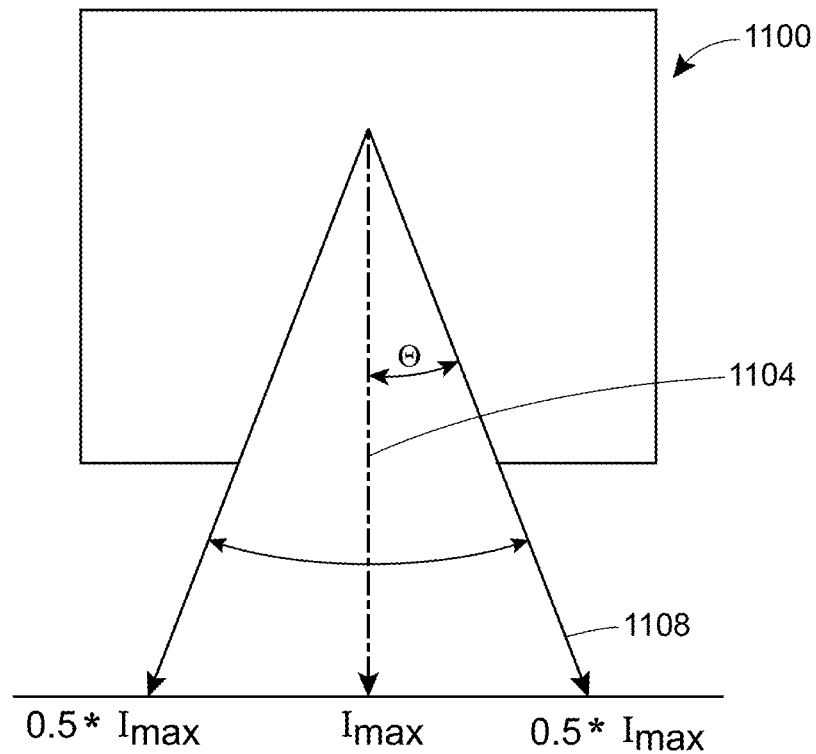
FIG. 11A illustrates one example of a distribution of radiometric power by a lighting device constructed in accordance with the teachings of the present disclosure.

FIG. 11A illustrates one example of a distribution of the radiometric power output by a lighting device 1100, which takes the form of any one of the lighting devices 104, 200, 500, 600 described herein. As illustrated in FIG. 11A, the radiometric power is at a maximum value along a center axis 1104 of the light distribution from the lighting device 100, while the radiometric power along a line 1108 oriented at an angle $\theta$ from the center axis 1104 is equal to 50% of the maximum radiometric power value, so long as the radiometric power at the center axis 1104 and the radiometric power on the line 1108 are measured at equal distances from the lighting device 1100. The line 1108 in this version is oriented at an angle $\theta$ equal to 20 or 30 degrees from the center axis 1104, but may, in other versions, be oriented at a different angle $\theta$.

It will be appreciated that a lighting device such as one of the lighting devices 104, 200, 500, 600, 1100 described herein can distribute light within or throughout the environment 100 in any number of different ways, depending upon the given application. The lighting device can, for example, utilize a lambertian distribution 1120, an asymmetric distribution 1140, a downlight with cutoff distribution 1160, or a direct-indirect distribution 1180, as illustrated in FIGS. 11B-11E, respectively.

Figure 11B:
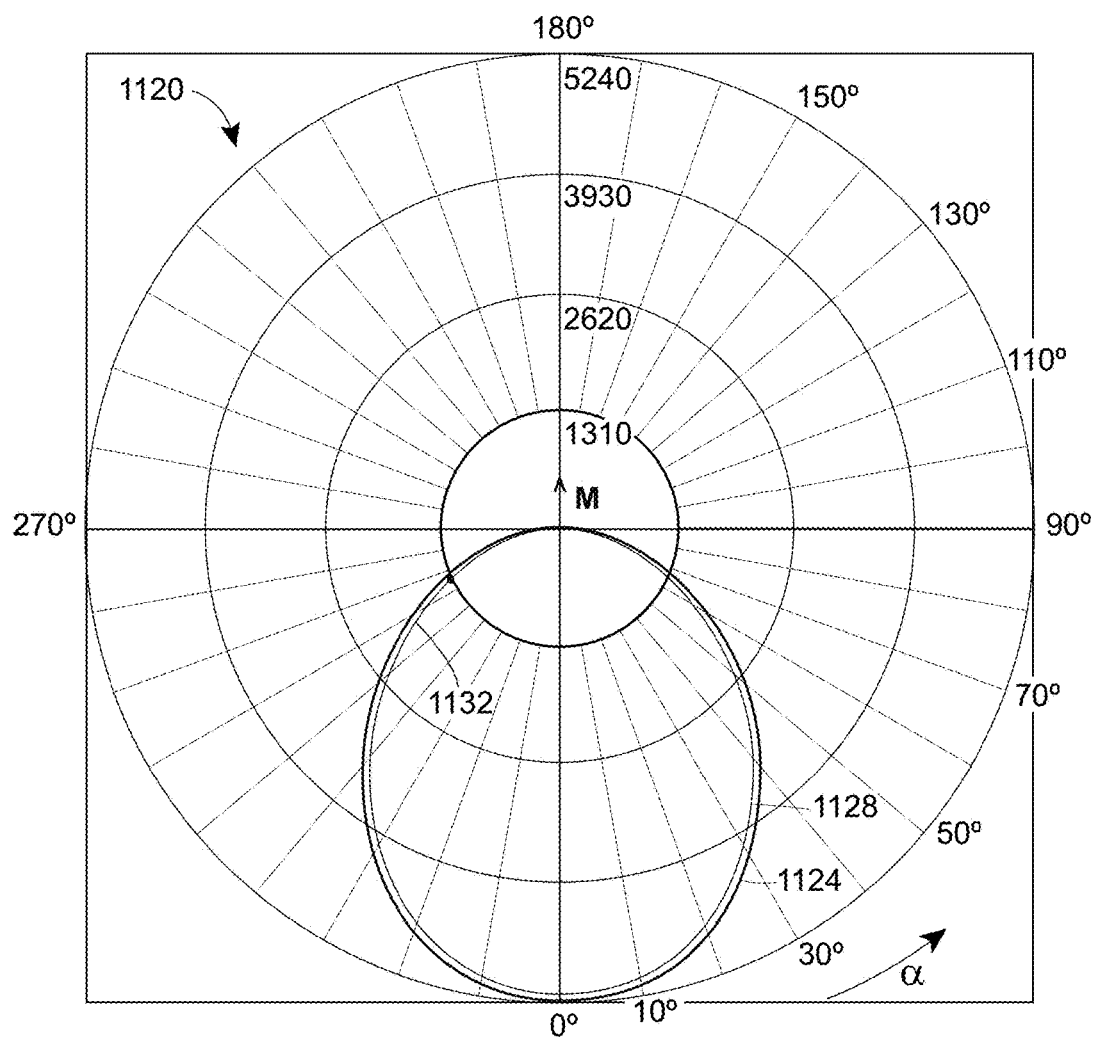
FIG. 11B illustrates a plot of one example of light distribution from a lighting device, constructed in accordance with the teachings of the present disclosure, as a function of the vertical angle from the horizontal.

The lambertian distribution plot 1120 illustrated in FIG. 11B takes the form of a two-dimensional polar graph that depicts a magnitude M of the intensity of the light output from a lighting device as a function of the vertical a from the horizontal. As shown in FIG. 11B, the lambertian distribution plot 1120 includes a first light distribution 1124 measured along a vertical plane through horizontal angles 0-180 degrees, a second light distribution 1128 measured along a vertical plane through horizontal angles 90-270 degrees, and a third light distribution 1132 measured along a vertical plane through horizontal angles 180-0 degrees. As illustrated by each of the first, second, and third light distributions 1124, 1128, and 1132, the magnitude M of light intensity is at its maximum value (in this example, 5240 candela) when the vertical angle α is equal to 0 degrees (i.e., nadir), such that the main beam angle, which corresponds to the vertical angle of highest magnitude, is equal to 0 degrees. The magnitude M then decreases as the vertical angle α moves from 0 degrees to 90 degrees.

Figure 11C:
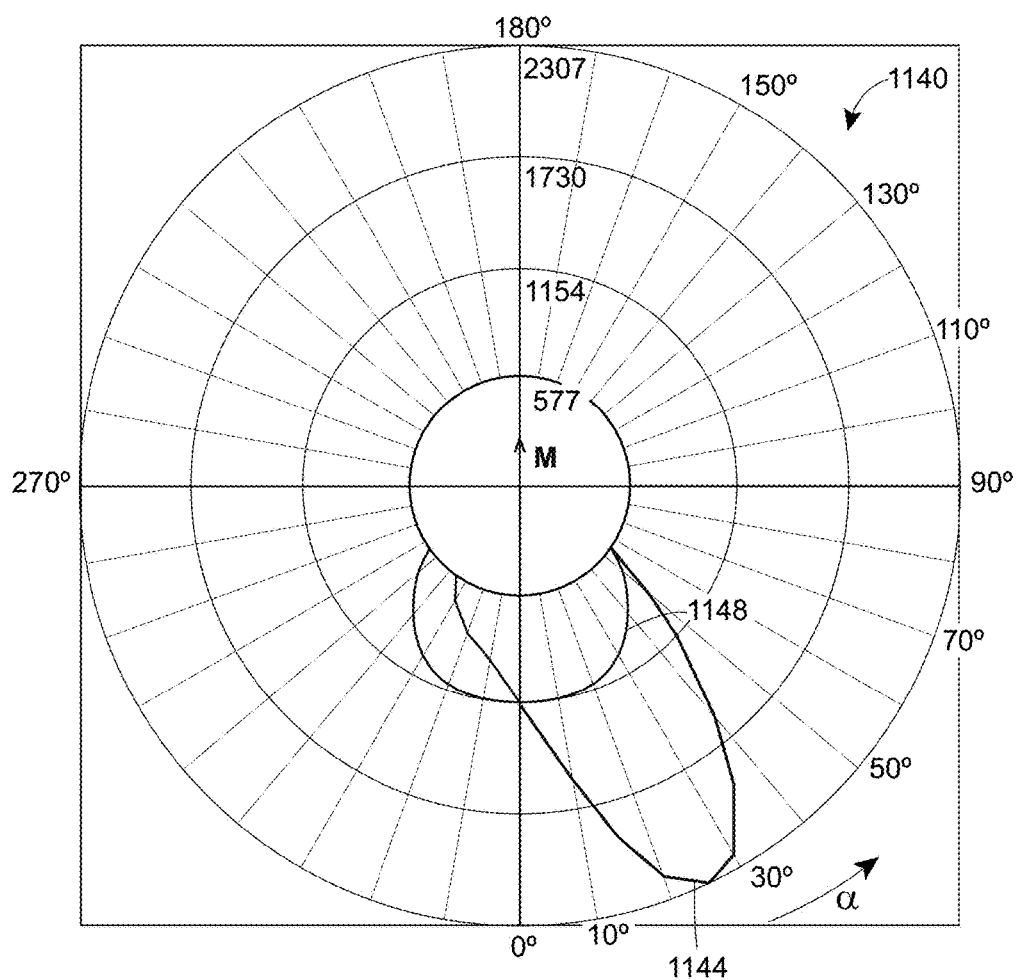
FIG. 11C illustrates a plot of another example of light distribution from a lighting device, constructed in accordance with the teachings of the present disclosure, as a function of the vertical angle from the horizontal.

The asymmetric distribution plot 1140 illustrated in FIG. 11C likewise takes the form of a two-dimensional polar graph that depicts the magnitude M of the intensity of the light output from a lighting device as a function of the vertical a from the horizontal. As shown in FIG. 11C, the asymmetric distribution plot 1140 includes a first light distribution 1144 measured along a vertical plane through horizontal angles between 0-180 degrees and a second light distribution 1148 measured along a vertical plane through horizontal angles between 90-270 degrees. As illustrated by the first and second light distributions 1144, 1148, light is distributed asymmetrically to one side of the lighting device, with the magnitude M of light intensity at its maximum value (in this example, 2307 candela) when the vertical angle α is equal to 25 degrees, such that the main beam angle, which corresponds to the vertical angle α of highest magnitude, is equal to 25 degrees. Such a distribution may, for example, be utilized in an environment 100 that features an operating table, so that the main beams of light from the lighting device are directed toward the operating table.

Figure 11D:
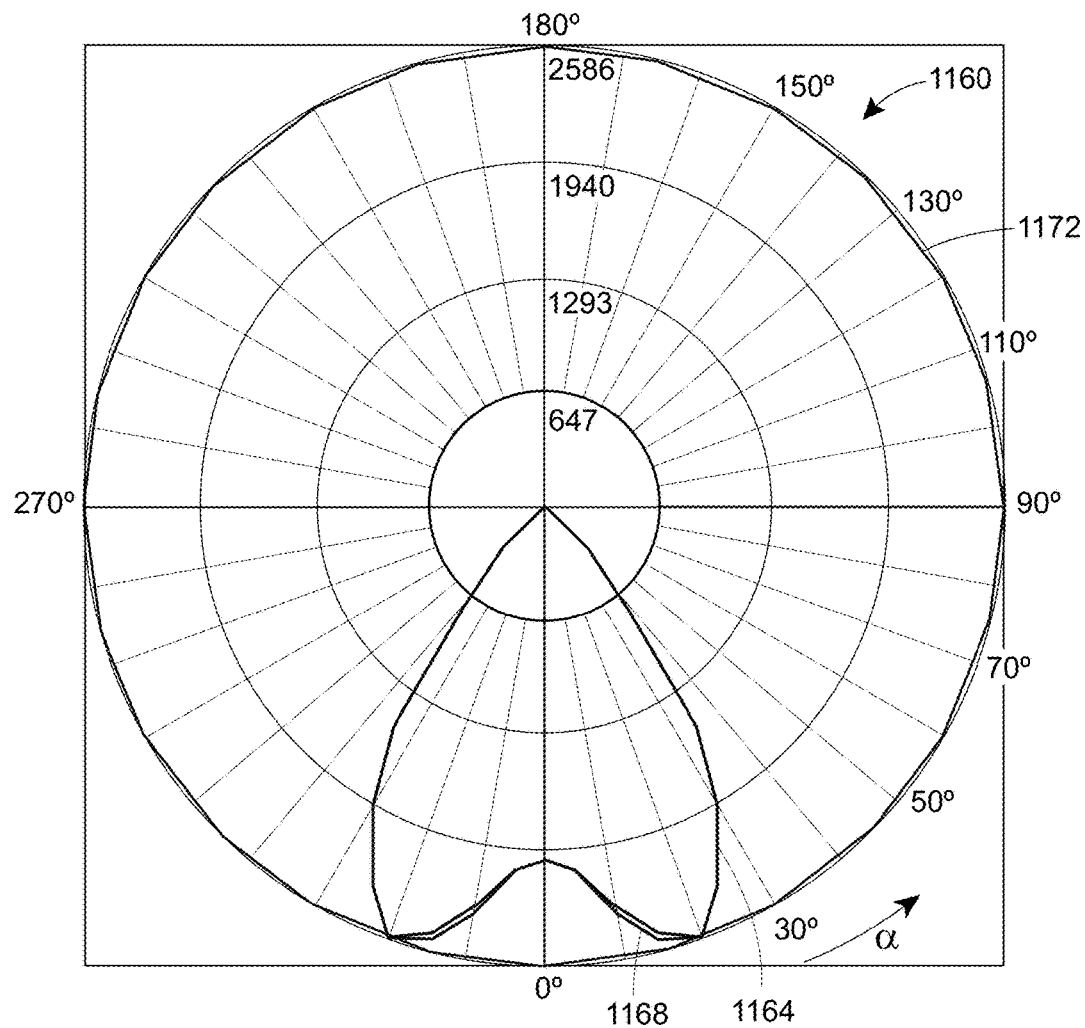
FIG. 11D illustrates a plot of another example of light distribution from a lighting device, constructed in accordance with the teachings of the present disclosure, as a function of the vertical angle from the horizontal.

The downlight with cutoff distribution plot 1160 illustrated in FIG. 11D also takes the form of a two-dimensional polar graph that depicts the magnitude M of the intensity of the light output from a recessed lighting device as a function of the vertical a from the horizontal. As shown in FIG. 11D, the distribution plot 1160 includes a first light distribution 1164 measured along a vertical plane through horizontal angles between 0-180 degrees, a second light distribution 1168 measured along a vertical plane through horizontal angles between 90-270 degrees, and a third light distribution 1172 measured along a horizontal cone through a vertical angle α of 20 degrees. As illustrated by the first, second, and third light distributions 1164, 1168, and 1172, the magnitude M of light intensity is at its maximum value (in this example, 2586 candela) when the horizontal angle is 60 degrees and the vertical angle α is equal to 20 degrees, and there is very minimal light intensity (i.e., the light is cutoff) above 45 degrees. The main beam angle, which corresponds to the vertical angle α of highest magnitude, is thus equal to 20 degrees, making this distribution appropriate for applications when, for example, an off-center but symmetrical distribution is desired. This type of distribution generally allows for greater spacing between adjacent lighting devices while maintaining a relatively uniform projection of light on the ground.

Figure 11E:
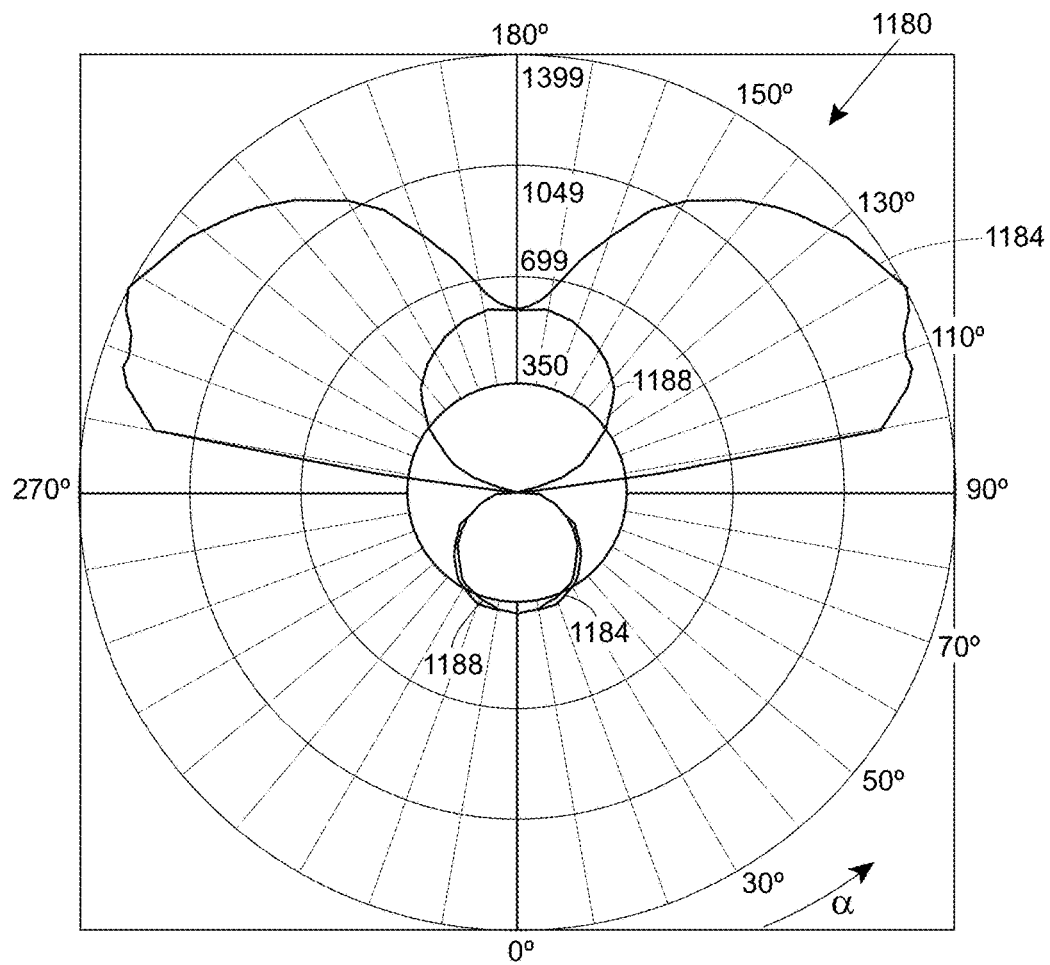
FIG. 11E illustrates a plot of another example of light distribution from a lighting device, constructed in accordance with the teachings of the present disclosure, as a function of the vertical angle from the horizontal.

The direct-indirect distribution plot 1180 illustrated in FIG. 11E also takes the form of a two-dimensional polar graph that depicts the magnitude M of the intensity of the light output from a lighting device as a function of the vertical a from the horizontal. As shown in FIG. 11E, the distribution plot 1180 includes a first light distribution 1184 along a vertical plane through horizontal angles between 90-270 degrees, and a second light distribution 1188 measured along a vertical plane through horizontal angles between 180-0 degrees. As illustrated by the first and second light distributions 1184 and 1168, the magnitude M of light intensity is at its maximum value (in this example, 1398 candela) when the horizontal angle is 90 degrees and the vertical angle α is equal to 117.5 degrees, and most (e.g., approximately 80%) of the light is directed upwards (as evidenced by the fact that the light intensity is greater at vertical angles α between 90 degrees and 270 degrees. The main beam angle, which corresponds to the vertical angle α of highest magnitude, is thus equal to 117.5 degrees, making this distribution appropriate for applications when, for example, the lighting device is suspended from a ceiling and utilizes the ceiling to provide light to the environment, which in turn provides a low-glare lighting to the environment.

FIGS. 11F-11I each depict a chart that details the luminous flux (measured in lumens) for the lambertian, asymmetric, downlight with cutoff, and direct-indirect distributions 1120, 1140, 1160, and 1180, respectively. More specifically, each chart details the integration of the luminous intensity over the solid angle of the respective distribution 1120, 1140, 1160, and 1180, for various zones of vertical angles α (i.e., the luminous flux).

Figure 12:
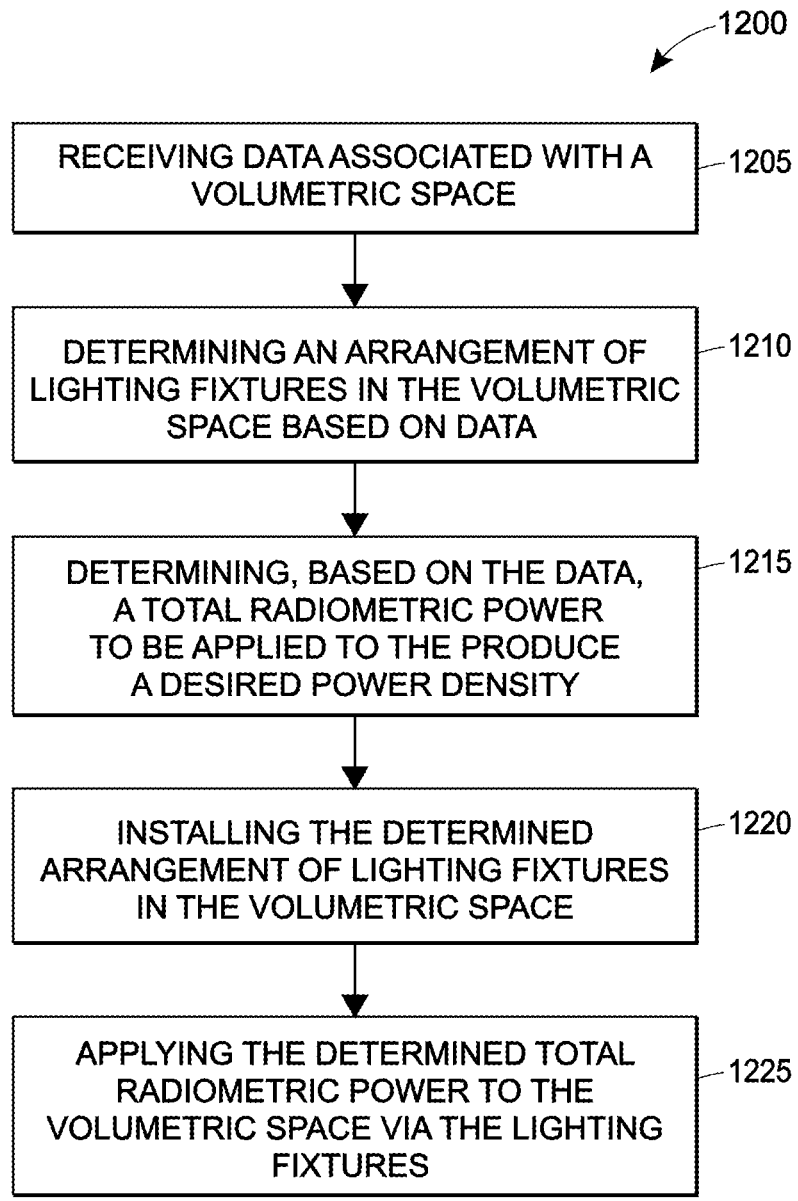
FIG. 12 is a flowchart of an exemplary method of providing doses of light sufficient to deactivate dangerous pathogens throughout a volumetric space over a period of time.

FIG. 12 depicts a flowchart of one method 1200 of providing doses of light sufficient to deactivate dangerous pathogens (e.g., MRSA bacteria) throughout a volumetric space (e.g., the environment 100) over a period of time (e.g., 24 hours). The method 1200 is implemented in the order shown, but may be implemented in or according to any number of different orders. The method 1200 may include additional, fewer, or different acts. For example, the first, second, third, and/or fourth data received in act 1205 may be received at different times prior to act 1220, with the receipt of data at different times constituting different acts. As another example, the acts 1205, 1210, and 1215 may be repeated a number of times before the act 1220 is performed.

The method 1200 begins when data associated with the volumetric space is received (act 1205). The data may include (i) first data associated with a desired illuminance level for the volumetric space, (ii) second data indicative of an estimated occupancy of the volumetric space over a pre-determined period of time, (iii) third data indicative of a length, width, and/or height of the volumetric space (one or more of the length, width, and/or height may be a default value, so need not be provided), and (iv) fourth data indicative of a preferred CCT for the volumetric space. While in this version the first, second, third, and fourth data is described as being received at the same time, these data can be received at different times. The desired illuminance level will vary depending upon the application and the size of the volumetric space, but may, for example, be 40-60 fc, 100-125 fc, 200-300 fc, or some other value or range of values. The estimated occupancy of the volumetric space over the pre-determined period of time generally relates to the amount of time per day that the volumetric space is occupied. Like the desired illuminance level, this will vary depending upon the application, but may be 4 hours, 6 hours, 8 hours, 12 hours, or some other period of time. The preferred CCT for the volumetric space will also vary depending upon the given application, but may, for example, be in a range of between approximately 1500 K and 7000 K, more particularly between approximately 1800 K and 5000 K.

The method 1200 includes determining an arrangement of one or more lighting fixtures to be installed in the volumetric space (act 1210). The determination is, in the illustrated method, based on the first data, though it can be made based on combinations of the first data, the second data, the third data, and/or the fourth data. The arrangement of one or more lighting fixtures generally includes one or more of any of the light fixtures described herein, e.g., the light fixture 200, light fixture 500, the light fixture 600, and/or one or more other light fixtures (e.g., one or more light fixtures configured to emit only disinfecting light). Thus, the arrangement of one or more lighting fixtures is configured to at least partially provide or output (e.g., emit) disinfecting light having a wavelength of between 380 nm and 420 nm, and more particularly between 400 nm and 420 nm. In some cases, the one or more lighting fixtures may also be configured to at least partially provide light having a wavelength of greater than 420 nm, such that the combined or blended light output of the lighting fixtures is a more aesthetically pleasing or unobjectionable than would otherwise be the case. The arrangement of one or more lighting fixtures may also include means for directing the disinfecting light, such as, for example, one or more reflectors, one or more diffusers, and one or more lenses positioned within or outside of the lighting fixtures. The arrangement of one or more lighting fixtures may optionally include a means for managing heat generated by the one or more lighting fixtures, such that heat-sensitive components in the one or more lighting fixtures can be protected. The means for managing heat may, for example, take the form of one or more heat sinks and/or may involve utilizing a switching circuit that, when a lighting fixture that utilizes two light-emitting devices is employed, prevents the two circuits for the light-emitting devices from being energized at the same time during use. In some cases, a thermal cutoff may be added to prevent the lighting fixture(s) from overheating.

The method 1200 also includes determining a total radiometric power to be applied to the volumetric space via the one or more lighting fixtures so as to produce a desired power density at any exposed surface (i.e., unshielded surface) within the volumetric space during the period of time (act 1215). The determination is, in the illustrated method, based on the second data and third data, though it can be made based on combinations of the first data, the second data, the third data, and/or the fourth data. As discussed above, the desired power density may be or include a minimum integrated irradiance equal to 0.01 mW/cm$^2$, 0.02 mW/cm$^2$, 0.05 mW/cm$^2$, 0.1 mW/cm$^2$, 0.15 mW/cm$^2$, 0.20 mW/cm$^2$, 0.25 mW/cm$^2$, 0.30 mW/cm$^2$, or some other value greater than 0.01 mW/cm$^2$. The minimum integrated irradiance may be measured from any unshielded point in the volumetric space, a distance of 1.5 m from any external-most luminous surface of the lighting device, nadir, or some other point or surface in the volumetric space. In this manner, dangerous pathogens in the volumetric space are effectively deactivated.

In one example, the total radiometric power to be applied to the volumetric space can be determined according to the following formula: Total radiometric power=(Minimum integrated irradiance (mW/cm$^2$)*Duration (fractional day))/Volume of volumetric space (ft$^3$), where the duration represents the amount of time per day that the volumetric space is to be occupied, and where the volume of the volumetric space is calculated by multiplying the length, height, and width of the volumetric space.

In some cases, e.g., when the arrangement of one or more lighting fixtures includes one or more lighting fixtures, such as the lighting fixtures 500, that are operable in different modes, the total radiometric power may be calculated for each of the modes and then summed to produce the total radiometric power to be applied to the volumetric space.

Once the total radiometric power to be applied to the volumetric space has been determined, the determined total may be compared to other applications (i.e., other volumetric spaces) for which disinfection levels have actually been measured, so as to verify that the total determined radiometric power for the volumetric space will be sufficient to deactivate dangerous pathogens.

The method 1200 then includes installing the determined arrangement of lighting fixtures in the volumetric space (act 1220), which can be done in any known manner, such that the determined total radiometric power can be applied to the volumetric space via the one or more lighting fixtures. The method 1200 optionally includes the act of applying the determined total radiometric power to the volumetric space via the one or more lighting fixtures (act 1225). By applying the determined total radiometric power, which is done without using any photosensitizers or reactive agents, produces the desired power density within the volumetric space during the period of time. In turn, dangerous pathogens within the volumetric space are, over the designated period of time, deactivated by the specially arranged and configured lighting fixtures.

In some cases, act 1225 may also involve controlling the one or more light fixtures, which may done via one or more controllers (e.g., the controller 120, the controller 520) communicatively connected to the light fixtures. More specifically, the wavelength, the intensity, the bandwidth, or some other parameter of the disinfecting light (e.g., the light having a wavelength of between 400 nm and 420 nm) may be controlled or adjusted. This may be done automatically, e.g., when the one or more controllers detect, via one or more sensors, that the wavelength, the intensity, the bandwidth, or some other parameter of the disinfecting light has strayed, responsive to a control signal received from a central controller located remotely from the one or more lighting fixtures, and/or responsive to an input received from a user or operator of the lighting fixtures (e.g., entered via one of the client devices 70). In one example, the one or more light fixtures can be controlled responsive to new or altered first, second, third, and/or fourth data being received and/or detected (e.g., via a photo controller). In any event, such control or adjustment helps to maintain the desired power intensity, such that the one or more lighting fixtures continue to effectively deactivate dangerous pathogens throughout the volumetric space.

It will be appreciated that the volumetric space may vary in size depending upon the given application. As an example, the volumetric space may have a volume up to and including 25,000 ft$^3$ (707.92 m$^3$). In some cases, the volumetric space may be partially defined or bounded by a plane of the one or more lighting fixtures and a floor plane of the volumetric space. As an example, the volumetric space may be partially defined by an area that extends between 0.5 m below a plane of the one or more lighting fixtures and 24 in. (60.96 cm) above a floor plane of the volumetric space or an area that extends between 1.5 m below a plane of the one or more lighting fixtures and 24 in. (60.96 cm) above a floor plane of the volumetric space. The volumetric space may alternatively be defined by areas that are a different distance from the plane of the one or more lighting fixtures and/or the floor plane of the volumetric space.

Finally, it will be appreciated that the acts 1205, 1210, 1215, 1220, and 1225 of the method 1200 may be implemented by the server 66, one of the client devices 70, some other machine or device, a person, such as a user, a technician, an administrator, or operator, associated with the volumetric space, or combinations thereof.

Figure 13:
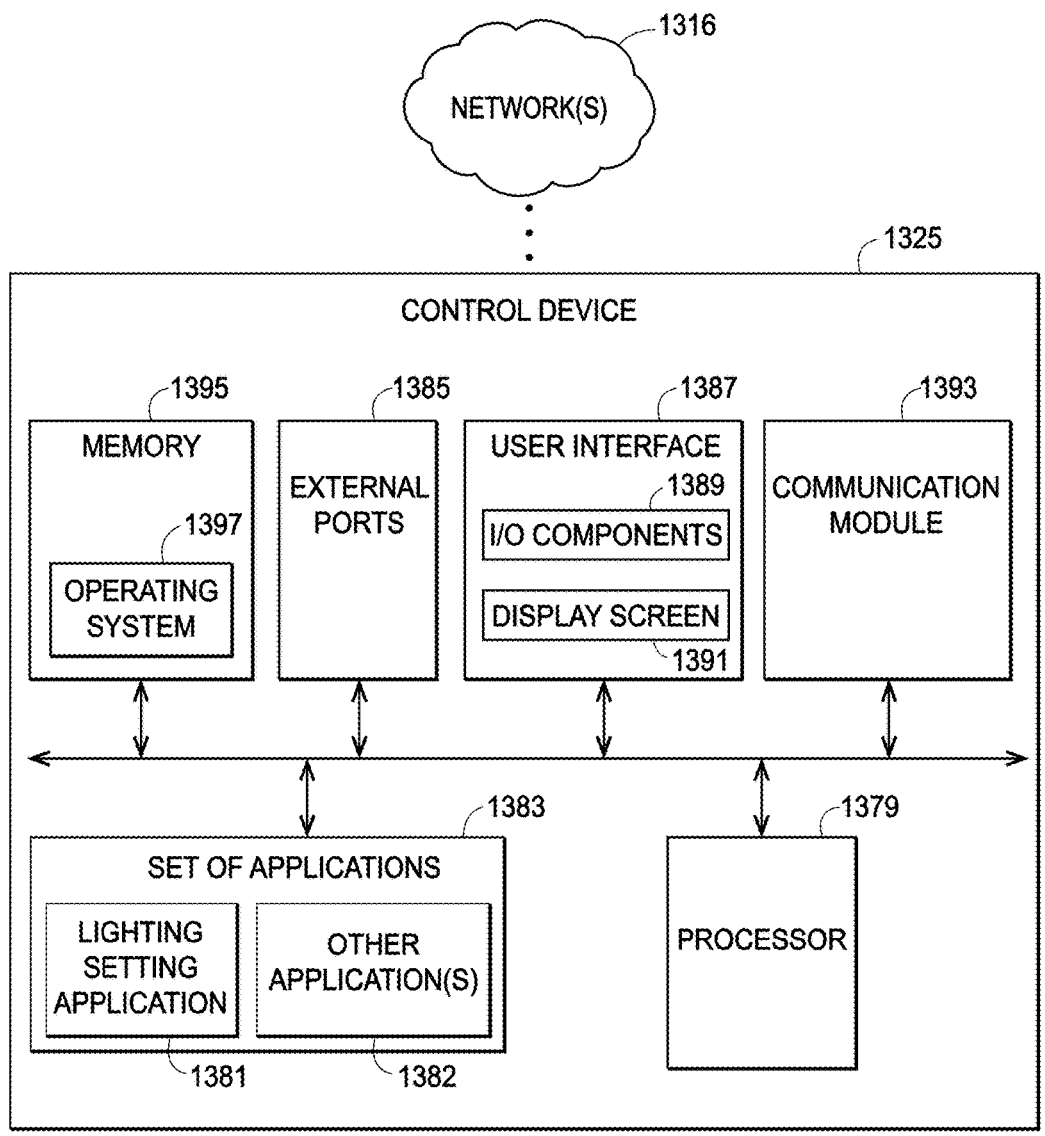
FIG. 13 is a schematic diagram of an exemplary version of a control device constructed in accordance with the teachings of the present disclosure.

FIG. 13 illustrates an example control device 1325 via which some of the functionalities discussed herein may be implemented. In some versions, the control device 1325 may be the server 66 discussed with respect to FIG. 1, the local controller 120 discussed with respect to FIG. 2, the dosing feedback system 124 discussed with respect to FIG. 2, the local controller 520 discussed with respect to FIG. 9D, the local controller 618, or any other control components (e.g., controllers) described herein. Generally, the control device 1325 is a dedicated machine, device, controller, or the like, including any combination of hardware and software components.

The control device 1325 may include a processor 1379 or other similar type of controller module or microcontroller, as well as a memory 1395. The memory 1395 may store an operating system 1397 capable of facilitating the functionalities as discussed herein. The processor 1379 may interface with the memory 1395 to execute the operating system 1397 and a set of applications 1383. The set of applications 1383 (which the memory 1395 may also store) may include a lighting setting application 1381 that is configured to generate commands or instructions to implement various lighting settings and transmit the commands/instructions to a set of lighting devices. It should be appreciated that the set of applications 1383 may include one or more other applications 1382.

Generally, the memory 1395 may include one or more forms of volatile and/or non-volatile, fixed and/or removable memory, such as read-only memory (ROM), electronic programmable read-only memory (EPROM), random access memory (RAM), erasable electronic programmable read-only memory (EEPROM), and/or other hard drives, flash memory, MicroSD cards, and others.

The control device 1325 may further include a communication module 1393 configured to interface with one or more external ports 1385 to communicate data via one or more networks 1316 (e.g., which may take the form of one or more of the networks 74). For example, the communication module 1393 may leverage the external ports 1385 to establish a WLAN for connecting the control device 1325 to a set of lighting devices and/or to a set of bridge devices. According to some embodiments, the communication module 1393 may include one or more transceivers functioning in accordance with IEEE standards, 3GPP standards, or other standards, and configured to receive and transmit data via the one or more external ports 1385. More particularly, the communication module 1393 may include one or more wireless or wired WAN, PAN, and/or LAN transceivers configured to connect the control device 1325 to the WANs, PANs, and/or LANs.

The control device 1325 may further include a user interface 1387 configured to present information to a user and/or receive inputs from the user. As illustrated in FIG. 13, the user interface 1387 includes a display screen 1391 and I/O components 1389 (e.g., capacitive or resistive touch sensitive input panels, keys, buttons, lights, LEDs, cursor control devices, haptic devices, and others).

In general, a computer program product in accordance with an embodiment includes a computer usable storage medium (e.g., standard random access memory (RAM), an optical disc, a universal serial bus (USB) drive, or the like) having computer-readable program code embodied therein, wherein the computer-readable program code is adapted to be executed by the processor 1379 (e.g., working in connection with the operating system 1397) to facilitate the functions as described herein. In this regard, the program code may be implemented in any desired language, and may be implemented as machine code, assembly code, byte code, interpretable source code or the like (e.g., via C, C++, Java, Actionscript, Objective-C, Javascript, CSS, XML, and/or others).

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still cooperate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as examples and does not describe every possible embodiment, as describing every possible embodiment would be impractical, if not impossible. One could implement numerous alternate embodiments, using either current technology or technology developed after the filing date of this application.

What is claimed:
1. A lighting device configured to deactivate MRSA bacteria in an environment, the lighting device comprising:
    at least one lighting element with a single light source configured to provide light, at least a first component of the light having a wavelength of about 405 nm, and at least a second component of the light having a wavelength of greater than 420 nm,
wherein the first component of light has a minimum integrated irradiance of 0.01 mW/cm² measured from any unshielded point in the environment that is 1.5 m from any point on any external-most luminous surface of the lighting device.

2. The lighting device of claim 1, wherein the minimum integrated irradiance is equal to 0.10, 0.15, 0.20, 0.25, or 0.30 mW/cm².

3. The lighting device of claim 1, wherein a radiometric power at 20 degrees from a center axis of light distribution is equal to 50% of a radiometric power at the center axis of light distribution, wherein the radiometric power at 20 degrees and the radiometric power at the center axis are measured at equal distances from the at least one lighting element.

4. The lighting device of claim 3, wherein a radiometric power at 30 degrees from a center axis of light distribution is equal to 50% of a radiometric power at the center axis of light distribution, wherein the radiometric power at 30 degrees and the radiometric power at the center axis are measured at equal distances from the at least one lighting element.

5. The lighting device of claim 1, wherein the at least one lighting element comprises at least one light-emitting diode (LED).

6. The lighting device of claim 5, further comprising a means for maintaining a junction temperature of the at least one LED below a maximum operating temperature of the at least one LED.

7. The lighting device of claim 1, wherein the light emitted by the at least one lighting element has a luminous flux above a cone angled downward from the lighting device at 60 degrees circumferentially around nadir of the lighting device, the luminous flux being greater than 15%, 20%, 25%, or 30% of a total luminous flux of the light emitted by the at least one lighting element.

8. The lighting device of claim 1, further comprising at least one additional lighting element configured to emit light having a wavelength of about 405 nm.

9. The lighting device of claim 1, further comprising a controller configured to control the at least one lighting element responsive to a control signal received from a user of the lighting device or a central controller located remotely from the lighting device.

10. The lighting device of claim 1, wherein the at least one lighting element comprises at least one light-emitting diode (LED) and at least one phosphor element covering or arranged proximate to the at least one LED, the at least one phosphor element configured to produce the second component of the light emitted by the at least one lighting element.

11. The lighting device of claim 1, wherein the first component of the light comprises at least 4 watts of the light having the wavelength of about 405 nm.

12. A lighting device configured to deactivate MRSA bacteria in an environment, the lighting device comprising:
at least one light-emitting element with a single light source configured to emit light having a wavelength of about 405 nm;
at least one light converting element,
wherein at least a first component of the light emitted by the at least one light-emitting element travels through the at least one light converting element without alteration, and at least a second component of the light emitted by the at least one light-emitting element is converted into light having a wavelength of greater than 420 nm, and
wherein the first component of the light has a minimum integrated irradiance of 0.01 mW/cm² measured from any unshielded point in the environment that is 1.5 m from any point on any external-most luminous surface of the lighting device.

13. The lighting device of claim 12, wherein the minimum integrated irradiance is equal to 0.05 0.10, 0.15, 0.20, 0.25, or 0.30 mW/cm².

14. The lighting device of claim 12, wherein a radiometric power at 20 degrees from a center axis of light distribution is equal to 50% of a radiometric power at the center axis of light distribution, wherein the radiometric power at 20 degrees and the radiometric power at the center axis are measured at equal distances from the at least one light-emitting element.

15. The lighting device of claim 12, wherein the light emitted by the at least one light-emitting element has a luminous flux above a cone angled downward from the lighting device at 60 degrees circumferentially around nadir of the lighting device, the luminous flux being greater than 15%, 20%, 25%, or 30% of a total luminous flux of the light emitted by the at least one light-emitting element.

16. The lighting device of claim 12, wherein the at least one light-emitting element comprises at least one light-emitting diode, and the lighting device further comprising means for maintaining a junction temperature of the at least one light-emitting diode below a maximum operating temperature of the at least one light-emitting diode.

17. The lighting device of claim 12, further comprising a controller configured to control the at least one light-emitting element responsive to a control signal received from a user of the lighting device or a central controller located remotely from the lighting device.

18. The lighting device of claim 12, wherein the at least one light converting element either covers the at least one light-emitting element or is remote from the at least one light-emitting element.

19. The lighting device of claim 12, wherein the at least one light converting element comprises at least one phosphor coating.

20. The lighting device of claim 12, wherein the first component of the light comprises at least 4 watts of the light having the wavelength of about 405 nm.

21. A method of deactivating MRSA bacteria in an environment, the method comprising:
providing light from at least one lighting element of a lighting device installed in the environment, the light provided by the at least one lighting element is produced from a single light source, at least a first component of the light has a wavelength of about 405 nm and has a minimum integrated irradiance of 0.01 mW/cm² measured from any unshielded point in the environment that is 1.5 m from any point on any external-most luminous surface of the lighting device, and wherein at least a second component of the light has a wavelength of greater than 420 nm.

\* \* \* \* \*